(12) United States Patent
Lee et al.

(10) Patent No.: US 11,738,191 B2
(45) Date of Patent: Aug. 29, 2023

(54) MEDICAL DEVICE APPARATUS, SYSTEM, AND METHOD

(71) Applicants: Samsung Electronics Co., Ltd., Suwon-si (KR); Samsung Life Public Welfare Foundation, Seoul (KR)

(72) Inventors: Hyungwoo Lee, Seoul (KR); Duk Lyul Na, Seoul (KR); Dae Won Seo, Seoul (KR); Young Min Shon, Seoul (KR); Jin San Lee, Seoul (KR); Woo Ram Jung, Seoul (KR); Sang Joon Kim, Hwaseong-si (KR); Joonseong Kang, Suwon-si (KR); Wonseok Lee, Yongin-si (KR)

(73) Assignees: Samsung Electronics Co., Ltd., Suwon-si (KR); Samsung Life Public Welfare Foundation, Seoul (KR)

( * ) Notice: Subject to any disclaimer, the term of this patent is extended or adjusted under 35 U.S.C. 154(b) by 1088 days.

(21) Appl. No.: 16/189,177

(22) Filed: Nov. 13, 2018

(65) Prior Publication Data

US 2019/0175902 A1    Jun. 13, 2019

(30) Foreign Application Priority Data

Dec. 12, 2017   (KR) .......................... 10-2017-0170762

(51) Int. Cl.
*A61N 1/05*        (2006.01)
*G06F 3/01*        (2006.01)
(Continued)

(52) U.S. Cl.
CPC .......... *A61N 1/0529* (2013.01); *A61B 5/0031* (2013.01); *A61B 5/4064* (2013.01);
(Continued)

(58) Field of Classification Search
CPC ... A61B 5/0031; A61B 5/4064; A61B 5/4836; A61B 5/0006; A61B 5/291; A61B 5/293;
(Continued)

(56) References Cited

U.S. PATENT DOCUMENTS 9,278,208 B1 *   3/2016  Gilson ................ A61B 5/4836
2005/0119713 A1  6/2005  Whitehurst et al.
(Continued)

FOREIGN PATENT DOCUMENTS

CN         104096313 A     10/2014
KR    10-2008-0100564 A    11/2008
(Continued)

OTHER PUBLICATIONS

Partial European Search Report dated Feb. 1, 2019 in counterpart European Application No. 18209139.7 (10 pages in English).
(Continued)

*Primary Examiner* — Kaylee R Wilson
*Assistant Examiner* — Raymond P Dulman
(74) *Attorney, Agent, or Firm* — NSIP Law

(57) ABSTRACT

Disclosed are a medical device apparatus, system, and method. A method includes receiving biometric information, by an external device external to a body of a user, of the user from an internal device within the body of the user, and wirelessly transmitting stimulus information configured to specify a stimulus based on the biometric information, and power to the internal device configured to drive the internal device and to apply the stimulus in response to the transmitted stimulus information. A method also includes wirelessly transmitting, from an internal device in a body of a user, biometric information of the user to an external device located outside the body of the user, and wirelessly receiving from the external device stimulus information configured to specify a stimulus, and power configured to drive the
(Continued)

internal device and to apply the stimulus to the user in response to the received stimulus information.

4 Claims, 21 Drawing Sheets

(51) Int. Cl.
    *A61B 5/00*     (2006.01)
    *A61N 1/36*     (2006.01)
    *A61N 1/378*     (2006.01)
    *H02J 50/10*     (2016.01)
    *A61N 1/372*     (2006.01)
    *A61B 5/053*     (2021.01)
    *A61B 5/01*     (2006.01)
    *A61B 5/30*     (2021.01)
    *A61B 5/291*     (2021.01)
    *A61B 5/316*     (2021.01)
    *A61B 5/375*     (2021.01)

(52) U.S. Cl.
    CPC ........ *A61B 5/4836* (2013.01); *A61N 1/36135* (2013.01); *G06F 3/015* (2013.01); *A61B 5/0006* (2013.01); *A61B 5/0008* (2013.01); *A61B 5/01* (2013.01); *A61B 5/053* (2013.01); *A61B 5/291* (2021.01); *A61B 5/30* (2021.01); *A61B 5/316* (2021.01); *A61B 5/375* (2021.01); *A61B 2560/0219* (2013.01); *A61N 1/36064* (2013.01); *A61N 1/36103* (2013.01); *A61N 1/3787* (2013.01); *A61N 1/37247* (2013.01); *A61N 1/37264* (2013.01); *H02J 50/10* (2016.02)

(58) Field of Classification Search
    CPC ............ A61B 5/369; A61B 2560/0219; A61N 1/0529
    See application file for complete search history.

(56) References Cited

U.S. PATENT DOCUMENTS

2005/0165458 A1    7/2005  Boveja et al.
2007/0168222 A1*  7/2007  Hoyme ................ A61B 5/0022 600/300
2007/0255319 A1*  11/2007  Greenberg ......... A61N 1/36142 607/2
2009/0292336 A1*  11/2009  Nishida ................ A61N 1/3787 607/45
2010/0168545 A1*  7/2010  Kamath ............... A61B 5/1473 600/365
2010/0274101 A1*  10/2010  Lin .................... G01N 33/6893 600/301
2011/0301668 A1*  12/2011  Forsell ................ A61N 1/3787 607/60
2011/0319785 A1   12/2011  Snyder et al.
2014/0094674 A1   4/2014  Nurmikko et al.
2014/0316309 A1   10/2014  Seo et al.
2014/0371802 A1   12/2014  Mashiach et al.
2015/0066104 A1   3/2015  Wingeier et al.
2016/0184596 A1   6/2016  Fried et al.
2017/0108926 A1   4/2017  Moon et al.
2017/0199569 A1   7/2017  Cruz-Hernandez
2019/0143119 A1*  5/2019  Dzirasa .............. A61N 1/36096 607/2

FOREIGN PATENT DOCUMENTS

| KR | 10-1136880 B1 | 4/2012 | |
| KR | 10-2012-0087633 A | 8/2012 | |
| KR | 10-2016-0046887 A | 4/2016 | |
| KR | 10-2016-0099174 A | 8/2016 | |
| KR | 10-2017-0051699 A | 5/2017 | |
| KR | 10-1747023 B1 | 6/2017 | |
| WO | WO-2011038767 A1 * | 4/2011 | ........... A61B 5/0482 |
| WO | WO 2017/091828 A1 | 6/2017 | |

OTHER PUBLICATIONS

Korean Office Action dated Aug. 24, 2021 in counterpart Korean Patent Application Number 10-2017-0170762 (8 pages in English and 10 pages in Korean).

Extended European Search Report dated Jun. 21, 2019, in counterpart European Application No. 18209139.7 (10 pages in English).

* cited by examiner

FIG. 15
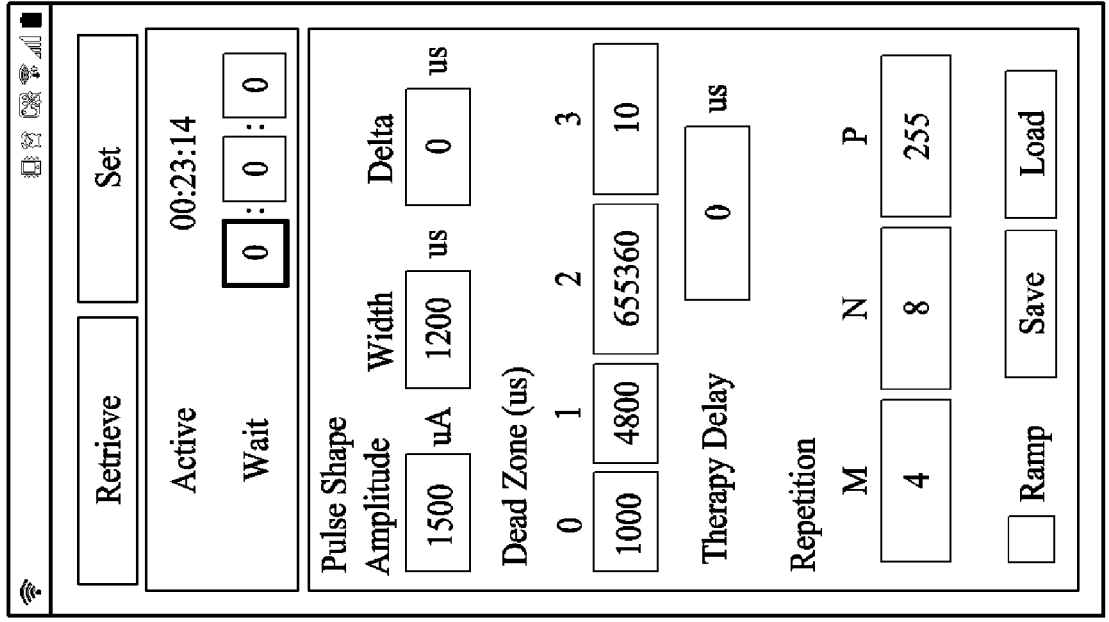
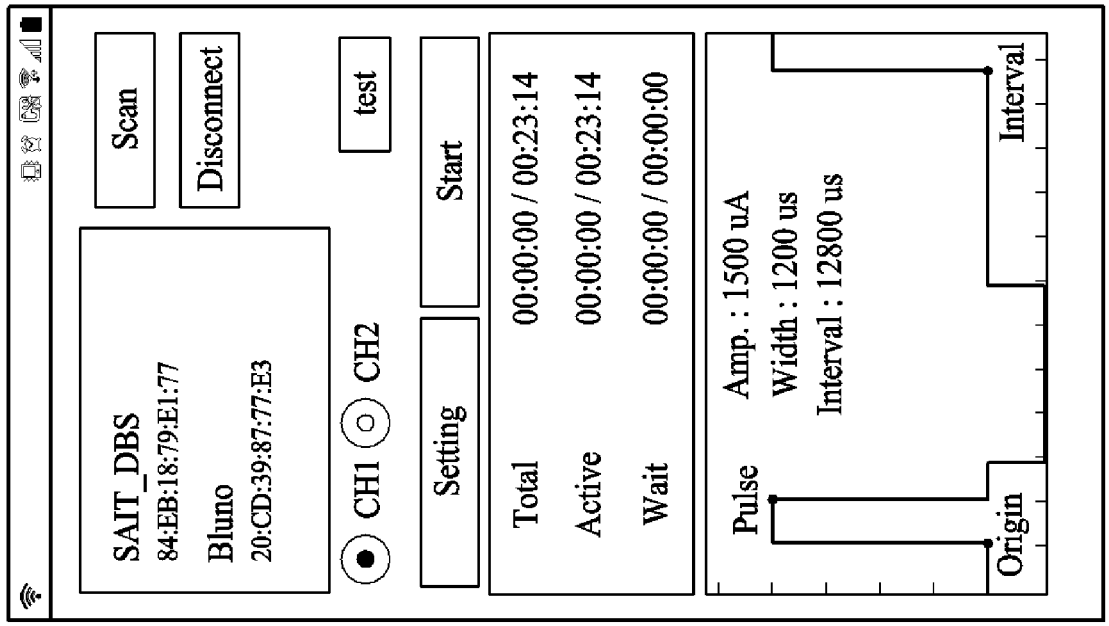

MEDICAL DEVICE APPARATUS, SYSTEM, AND METHOD

CROSS-REFERENCE TO RELATED APPLICATIONS

This application claims the benefit under 35 USC § 119(a) of Korean Patent Application No. 10-2017-0170762 filed on Dec. 12, 2017 in the Korean Intellectual Property Office, the entire disclosure of which is incorporated herein by reference for all purposes.

BACKGROUND

1. Field

The following description relates to a medical device apparatus, system, and method

2. Description of Related Art

An implantable medical device is a device that is inserted into the body and used for diagnosis and treatment of diseases. The implantable medical device may include, for example, a deep brain stimulator and a nerve stimulator. The implantable medical device may be inserted in the body for a long period of time to detect a disease or alleviate a symptom of the disease.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In one general aspect, a medical device method includes receiving biometric information, by an external device external to a body of a user, of the user from an internal device within the body of the user, and wirelessly transmitting stimulus information configured to specify a stimulus based on the biometric information, and power to the internal device configured to drive the internal device and to apply the stimulus in response to the transmitted stimulus information.

The method may further include determining whether to apply the stimulus to the user based on the biometric information, where the wirelessly transmitting of the stimulus information and the wirelessly transmitting of the power may be respectively performed dependent on a result of the determining.

The determining of whether to apply the stimulus to the user may include determining to apply the stimulus in response to detection of an abnormal symptom in the user based on the biometric information.

The determining of whether to apply the stimulus to the user may include determining not to apply the stimulus to the user in response to a determination that the body of the user is damaged or that the internal device is malfunctioning based on the biometric information.

The method may further include receiving control information from a user terminal controlled by the user, and determining the stimulus information based on the control information.

The control information may include at least one of first control information determined by a first feedback loop including the internal device, the external device, and the user terminal, and second control information determined by a second feedback loop including the internal device, the external device, the user terminal, and an electronic device controlled by a medical specialist.

The first control information may include information indicating a stimulus pattern selected from at least one first stimulus pattern determined in association with the first feedback loop.

The second control information may include at least one of information indicating a stimulus pattern selected from at least one second stimulus pattern determined in association with the second feedback loop, and information indicating a stimulus pattern generated in real time based on the biometric information.

The control information may be set by the user or a medical specialist diagnosing the user.

The determining of the stimulus information based on the control information may include resetting the stimulus information based on control information determined by a medical specialist diagnosing the user.

The determining of the stimulus information based on the control information may include resetting the stimulus information based on the control information determined by a medical specialist diagnosing the user in response to a current state of the user based on the biometric information.

The wirelessly transmitting of the stimulus information and the wirelessly transmitting of the power may be respectively performed dependent on the external device being within at least a proximity to the internal device enabling power and stimulus information transfer from the external device to the internal device.

The wirelessly transmitting of the stimulus information and the wirelessly transmitting of the power may be respectively performed using a coil of the external device, the coil corresponding to a coil of the internal device.

The receiving of the biometric information of the user may include receiving the biometric information of the user from the internal device while the power for driving the internal device is transmitted to the internal device from the external device.

The stimulus information may include information on any one or any combination of an intensity, a duration, an interval, and a repetition count of a pulse applied to the user.

The biometric information may include information on any one or any combination of a contact impedance, a humidity, a temperature, and an electroencephalogram (EEG) signal of the user.

The method may further include transmitting the received biometric information to a user terminal controlled by the user while the external device is connected to the user terminal.

The method may be an operating method of a medical device system that includes the internal device and the external device, where the method may further include controlling the internal device to collect the biometric information, and controlling the internal device to apply the stimulus.

The medical device system may further include a user terminal, where the method may further include determining control information set by a technician provided communication with the user terminal, and respectively controlling the wirelessly transmitting of the stimulus and the wirelessly transmitting of the power to the internal device by the external device based on the determining and/or the control information as provided by the user terminal.

The medical device system may further include an electronic device that includes a user interface to set the control information based on input by the technician to the user interface.

In one general aspect, provided is a non-transitory computer-readable storage medium storing instructions that, when executed by a processor, cause the processor to perform any one, any combination, or all operations and/or methods described herein.

In one general aspects, a medical device method includes wirelessly transmitting, from an internal device in a body of a user, biometric information of the user to an external device located outside the body of the user, and wirelessly receiving from the external device stimulus information configured to specify a stimulus, and power configured to drive the internal device and to apply the stimulus to the user in response to the received stimulus information.

The method may further include generating the stimulus using the received power based on the stimulus information, and applying the generated stimulus to the body of the user through a plurality of electrodes arranged at different positions in the body of the user.

The applying of the generated stimulus to the user through the plurality of electrodes arranged at the different positions in the body of the user may include applying the stimulus through a number of electrode pairs including an anode electrode and a cathode electrode, wherein the number of electrode pairs is equal to or greater than a number of channels of the stimulus.

The applying of the stimulus through the number of electrode pairs may include variably changing the anode electrode and the cathode electrode included in each of the electrode pairs based on the stimulus information.

The internal device may be located between a skull and a scalp of the user.

The stimulus information may indicate the stimulus based on the biometric information or control information transmitted to the external device from a user terminal controlled by the user.

The method may be an operating method of a medical device system that includes the internal device and the external device, where the method may further include controlling the external device to respectively wirelessly transmit the stimulus and the power to the internal device dependent on control information received by the external device.

The medical device system may further include a user interface configured to set the control information based on user input and/or provide the control information to the external device.

In one general aspect, a medical device method includes determining, by a user terminal, control information set by a user or a medical specialist diagnosing the user and configured to cause an external device that is located outside a body of the user to wirelessly transmit stimulus information and power to an internal device inserted in the body of the user in response to the external device receiving the control information, and transmitting, by the user terminal, the control information to the external device.

The control information may include at least one of first control information determined by a first feedback loop including the internal device, the external device, and the user terminal, and second control information determined by a second feedback loop including the internal device, the external device, the user terminal, and an electronic device controlled by the medical specialist.

The determining of the control information may include determining control information configured to cause application of a predetermined stimulus to the user at a point in time desired by the user in response to a request input from the user.

The method may further include receiving, from the external device, biometric information of the user sensed by the internal device, and transmitting the received biometric information to an electronic device controlled by the medical specialist diagnosing the user.

The determining of the control information may include receiving from the electronic device the control information set by the medical specialist diagnosing the user in response to a current state of the user indicated by the biometric information.

The method may be an operating method of a medical device system that includes the internal device, the external device, the user terminal, and the electronic device.

In one general aspect, a medical device method includes receiving, by an electronic device, biometric information of a user sensed by an internal device in a body of the user from a user terminal controlled by the user, determining control information, set by a medical specialist controlling the electronic device, configured to cause an external device that is located outside a body of the user to wirelessly transmit stimulus information and power to the internal device inserted in the body of the user in response the external device receiving the control information, and transmitting the control information to the user terminal.

The control information may include at least one of information used to select a stimulus pattern from at least one stimulus pattern determined in association with a feedback loop including the internal device, the external device, the user terminal, and the electronic device, and information indicating a stimulus pattern generated in real time in response to the received biometric information.

In one general aspect, a medical device system includes an external device located outside a body of a user, where the external device includes a data transceiver, a power transmitter, a coil connected to the data transceiver and the power transmitter, and a controller configured determine stimulus information based on biometric information of the user received from an internal device inserted in the body of the user by the data transceiver and cause the data transceiver and the power transmitter to transfer wirelessly using the coil the stimulus information and power to the internal device configured to drive the internal device and to apply a stimulus in response to the transmitted stimulus information. The system may further include the internal device.

In one general aspect, a medical device system includes an internal device located inside a body of a user, where the internal device includes a data transceiver, a power receiver, a coil connected to the data transceiver and the power receiver, a sensor configured to sense biometric information of the user, a stimulator, and a controller configured to cause the data transceiver to wirelessly transmit the biometric information to an external device located outside the body of the user using the coil, wirelessly receive from the external device using the data transceiver stimulus information configured to specify a stimulus, and wirelessly receive from the external device using the power receiver power configured to drive the sensor, stimulator, and controller, wherein the controller causes the stimulator to apply the stimulus to the body of the user in response to the received stimulus information. The system may further include the external device.

Other features and aspects will be apparent from the following detailed description, the drawings, and the claims.

BRIEF DESCRIPTION OF THE DRAWINGS

FIG. 15 illustrates an example of a stimulation interface.

Figure 1:
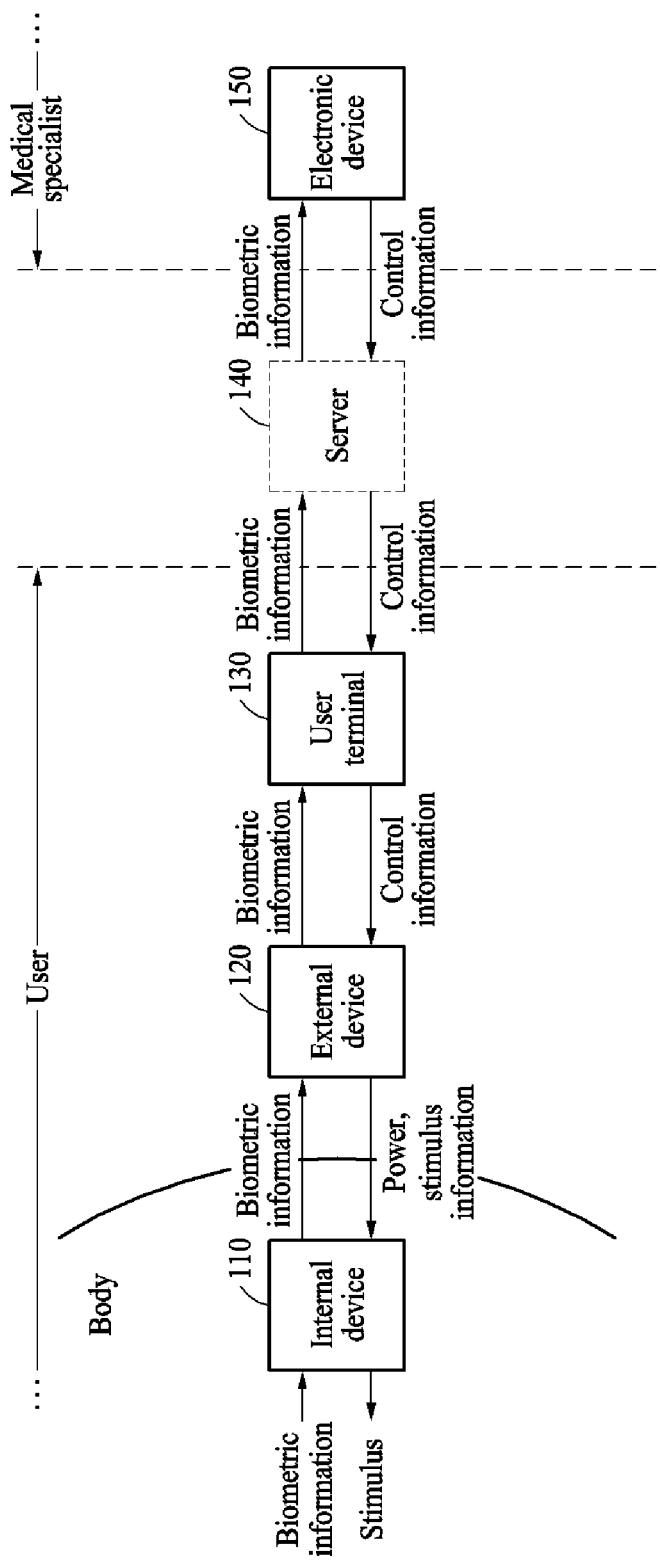
FIG. 1 illustrates an example of the relationship and communication paths between an internal device, an external device, a user terminal, a server, and an electronic device.

Throughout the drawings and the detailed description, unless otherwise described or provided, the same drawing reference numerals will be understood to refer to the same elements, features, and structures. The drawings may not be to scale, and the relative size, proportions, and depiction of elements in the drawings may be exaggerated for clarity, illustration, and convenience.

DETAILED DESCRIPTION

The following detailed description is provided to assist the reader in gaining a comprehensive understanding of the methods, apparatuses, and/or systems described herein. However, various changes, modifications, and equivalents of the methods, apparatuses, and/or systems described herein will be apparent after an understanding of the disclosure of this application. For example, the sequences of operations described herein are merely examples, and are not limited to those set forth herein, but may be changed as will be apparent after an understanding of the disclosure of this application, with the exception of operations necessarily occurring in a certain order. Also, descriptions of features that are known in the art may be omitted for increased clarity and conciseness.

The features described herein may be embodied in different forms, and are not to be construed as being limited to the examples described herein. Rather, the examples described herein have been provided merely to illustrate some of the many possible ways of implementing the methods, apparatuses, and/or systems described herein that will be apparent after an understanding of the disclosure of this application.

Although terms such as "first," "second," and "third" may be used herein to describe various members, components, regions, layers, or sections, these members, components, regions, layers, or sections are not to be limited by these terms. Rather, these terms are only used to distinguish one member, component, region, layer, or section from another member, component, region, layer, or section. Thus, a first member, component, region, layer, or section referred to in examples described herein may also be referred to as a second member, component, region, layer, or section without departing from the teachings of the examples.

Throughout the specification, when an element, such as a layer, a region, or a substrate, is described as being "on," "connected to," or "coupled to" another element, it may be directly "on," "connected to," or "coupled to" the other element, or there may be one or more other intervening elements. In contrast, when an element is described as being "directly on," "directly connected to," or "directly coupled to" another element, there are no other intervening elements.

The terminology used herein describes various examples only and is not intended to limit the disclosure. The articles "a," "an," and "the" are intended to include the plural forms, unless the context clearly indicates otherwise. The terms "comprises," "includes," and "has" specify the presence of stated features, numbers, operations, members, elements, and/or combinations thereof, but do not preclude the presence or addition of one or more other features, numbers, operations, members, elements, and/or combinations thereof.

Unless otherwise defined, all terms, including technical and scientific terms, used herein have the meaning as commonly understood by one of ordinary skill in the art to which this disclosure pertains and after an understanding of the disclosure of this application. Terms, such as those defined in commonly used dictionaries, are to be interpreted as having a meaning that is consistent with their meaning in the context of the relevant art and the disclosure of this application, and are not to be interpreted in an idealized or overly formal sense unless expressly so defined herein.

After gaining an understanding of the disclosure, if any one example of the detailed description of structures or functions are deemed to result in an ambiguous interpretation of an embodiment, such disclosure may be otherwise omitted for clarity.

In the following description, a user may be a patient suffering from a disease or a symptom which may be treated or alleviated by receiving a stimulus applied into the body of the user. A medical specialist diagnoses the user. For example, the medical specialist diagnoses a condition, a disease, or a symptom of the user based on biometric information of the use. The medical specialist remotely controls a stimulus applied to the user based on a diagnosis result. In this context, a medical specialist may be one or more of a doctor, a nurse, and a clinician.

FIG. 1 illustrates an example of a relationship between elements of a system 100, e.g., a medical device system.

Herein, the system 100 may include an internal device 110, an external device 120, a user terminal 130, a server 140, and/or an electronic device 150. Thus, while in an example, the system 100 includes the internal device 110, the external device 120, the user terminal 130, the server 140, and the electronic device 150, examples are not limited thereto. For example, in an example the system may include only the internal device 110, or only the external device 120, or a combination of the internal device 110 and the external device 120, i.e., one or more of any of the internal device 110, the external device 120, the user terminal 130, the server 140, and the electronic device 150, as non-limiting examples. Similarly, while respective described methods may also be respective methods of such an internal device, external device, user terminal, server, and electronic device, such examples also include such respective methods in various combinations, such as a method that includes the operations of an internal device and/or an external device, i.e., a method of one or more of any of the operations of such an internal device, external device, user terminal, server, and electronic device in various combinations, as non-limiting examples. Further, each of the internal device 110, the external device 120, the user terminal 130, and the electronic device 150 may also be respectively referred to as medical devices or medical device apparatuses that make up the example system 100.

As shown in FIG. 1, an internal device 110 is inserted in the body of the user. The internal device 110 senses biometric information of the user's body and wirelessly transmits the biometric information to an external device 120. Also, the internal device 110 may apply a stimulus to the user based on stimulus information wirelessly received from the external device 120. For example, the stimulus information is information about a stimulus to be applied to the user.

One example of a stimulus is an electrical stimulus applied using a plurality of electrodes (not shown). In this example, an electrode applies the electrical stimulus and induces bioactivity of brain tissue receiving the electrical stimulus. An action potential occurs in nerve and brain tissue receiving the stimulus such that other nerves connected to the stimulated nerve and brain tissue are sequentially activated in response to the action potential. One example of a technique for suppressing expression and deepening of brain disease using the electrical stimulus is referred to as brain stimulation.

The internal device 110 operates using power wirelessly transferred or received from the external device 120 instead of using other power sources, such as a battery or power supply. For example, wireless power may be transferred between the devices using the electromagnetic induction phenomenon. Size of the internal device 110 is minimized due to the absence of any battery, which may effectively reduce the burden on the user resulting from surgery inserting the internal device 110 into the body of the user. In addition, the internal device 110 may be used without need of any further maintenance, such as would be required with a battery. The internal device 110 senses biometric information of the user and applies a stimulus to the user based on the power received from the external device 120.

The external device 120 is located outside of the body of the user. In one example, the external device 120 is located outside the body of the user and in such proximity to the internal device 110 that data communication and power transfer are possible with the internal device. The external device 120 receives the biometric information of the user sensed by the internal device 110. The external device 120 wirelessly transmits the stimulus information about the stimulus to be applied to the user, in addition to the power that is transferred to drive the internal device 110 and apply the stimulus.

A user terminal 130 is a device controlled by the user. For example, the user terminal 130 is a smartphone, a mobile device, a wearable device, a tablet computer, a laptop computer, a personal computer, a smart home appliance, an intelligent vehicle, and/or other device operated by a user that is able to communication with the external device 120. The user terminal 130 communicates with the external device 120 through a wired or wireless network. The user terminal 130 receives the biometric information from the external device 120. The user terminal 130 also transmits control information to the external device 120. The control information transmitted to the external device 120 may be used by the external device 120 to determine the stimulus information. In one example, the control information is set in the user terminal 130 by the user.

A server 140 is connected to the user terminal 130 through the wired or wireless network and receives the biometric information from the user terminal 130. The server 140 records the biometric information received from the user terminal 130 in a database. In response to a request from the user terminal 130 or the electronic device 150, the server 140 transmits the recorded biometric information to the user terminal 130 or the electronic device 150. The server 140 also transmits the control information received from the electronic device 150 to the user terminal 130. In one example, the server 140 operates as a cloud database.

The use of the server 140 is not required and may be omitted in any particular application of the system 100. For example, the biometric information may be transmitted from the user terminal 130 directly to the electronic device 150 and stored in a memory in the electronic device 150. Also, the control information may be transmitted from the electronic device 150 to the user terminal 130.

The electronic device 150 is a device controlled by the medical specialist. For example, the electronic device 150 is a smartphone, a mobile device, a wearable device, a tablet computer, a laptop computer, a personal computer, a smart home appliance, an intelligent vehicle, and/or other device operated or controlled by the medical specialist. The electronic device 150 receives the biometric information from the user terminal 130 or the server 140 and provides the received biometric information to the medical specialist. The electronic device 150 transmits control information input from the medical specialist to the user terminal 130 or the server 140. In one example, the control information set by the medical specialist may have greater authority than the control information set by the user.

The following description will be based on an example in which the server 140 is absent. However, the description is also applicable to any implementation in which the server 140 is present by those skilled in the art without restrictions.

Figure 2:
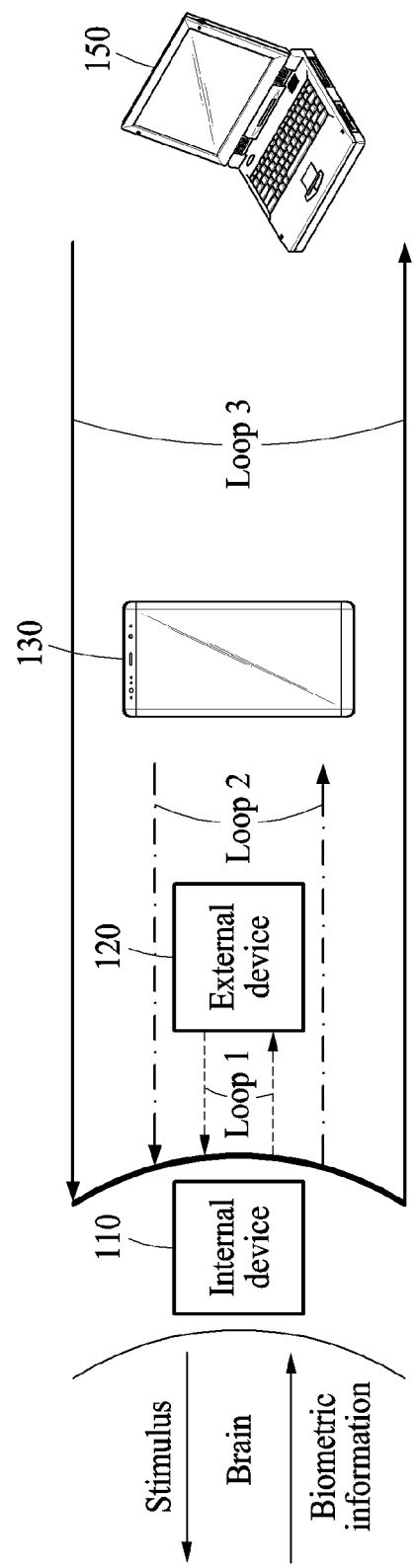
FIG. 2 illustrates an example of an operation of an internal device, an external device, a user terminal, and an electronic device for loop.

FIG. 2 illustrates an example of an operation of a system including an internal device, an external device, a user terminal, and an electronic device for each loop of the system.

Referring to FIG. 2, the system includes several loops formed between the devices of the system. As shown in FIG. 2, the system includes three loops, such as, for example, loop 1, loop 2, and loop 3. Each loop is formed using at least two devices of the system, such as the internal device 110, the external device 120, the user terminal 130, and the electronic device 150. Loop 1, Loop 2, and Loop 3 adaptively operate based on the severity of a disease or a symptom of a user, so that diagnosis, prescription, treatment, and the like suited to a condition of the user may be performed in real time.

Loop 1 includes the internal device 110 and the external device 120. For example, loop 1 operates when an urgent action is required to treat the disease or a symptom of the user. For example, it may be determined within the loop that a stimulus application is warranted immediately in response to sensed condition, such as for Epilepsy a stimulus may be applied upon detection of a seizure for immediate suppression. Loop 2 includes the internal device 110, the external device 120, and the user terminal 130. For example, loop 2 operates in response to a request from a user suffering from a chronic disease or symptom. For example, a user may request a stimulus to treat a user's depression at a desired time or setting. Loop 3 includes the internal device 110, the external device 120, the user terminal 130, and the electronic device 150. For example, loop 3 operates when a disease or a symptom of a user is regularly managed by the medical specialist. For example, a medical specialist may adjust or prescribe treatment in response to patient symptoms or detected patient state or biometric information in response to receive data or stored patient data. Each of the loops will now be described in greater detail in turn.

In loop 1, the internal device 110 senses biometric information of the user and transmits the biometric information to the external device 120. In this example, the internal device 110 is driven based on power wirelessly transmitted from the external device 120.

The external device 120 transmits stimulus information and power to the internal device 110 based on the biometric information received from the internal device 110. For example, the external device may transmit power to the internal device and receive biometric information from the internal device 110 in response. In this example, the external device 120 determines whether a stimulus should be applied to the user based on the biometric information received from the internal device 110.

In one example, when an abnormal symptom is detected based on the biometric information sensed by the internal device 110 from the user, the external device 120 determines that a stimulus should be applied to the user. For example, if the biometric information includes an electroencephalogram (EEG) signal, the external device 120 determines whether an abnormal EEG detected by the internal device 110 is a seizure precursor phenomenon based on the biometric information of a user suffering from epilepsy. In this example, when the external device determines the abnormal EEG is a seizure precursor phenomenon, the external device 120 determines that a stimulus should be applied to the user.

In another example, when it is determined that the internal device 110 is malfunctioning or the body of the user is damaged based on the biometric information, the external device 120 determines that a stimulus should not be applied to the user. The external device 120 determines whether the internal device 110 is malfunctioning or the body of the user is damaged based on any one or combination of a temperature, a humidity, and a contact impedance included in the biometric information.

For example, when the external device 120 verifies that at least one of the temperature and the humidity of the internal device 110 is beyond a threshold range, the external device 120 determines that the internal device 110 is malfunctioning or the body of the user is damaged (e.g., due to an abnormal temperature or an abnormal humidity). As a result, the external device 120 determines the stimulus should not be applied to the user. Also, when external device 120 verifies that the contact impedance between the internal device 110 and the body of the user is changed based on the biometric information, the external device 120 determines that the currently set stimulus is inappropriate for a disease or a symptom of the user. As a result, the external device 120 determines the stimulus should not be applied to the user.

In response to a determination that the stimulus should be applied to the user, the external device 120 transmits stimulus information corresponding to the stimulus to the internal device 110. In this example, the stimulus information is determined based on control information transmitted from the user terminal 130.

When it is determined that the stimulus should not be applied to the user, the external device 120 transmits at least one of the biometric information and a determination result to the user terminal 130 in a manner recognizable by the user. Also, the external device 120 transmits at least one of the biometric information and a determination result to the electronic device 150 in a manner recognizable to a medical specialist, such that the medical specialist is able to perform an appropriate diagnosis or prescription.

In loop 2, the user terminal 130 determines control information used to apply a predetermined stimulus to the user at a point in time desired by the user in response to a request input from the user. For example, a user suffering from a chronic disease, condition, or symptom, such as a depression and an insomnia may desire to receive a stimulus for alleviating the corresponding disease, condition, or symptom when the user is currently experiencing a need or desire for stimulus. Therefore, the user inputs a request for the desired stimulus to the user terminal 130.

In this example, the desired point in time includes various points in time, such as a current point in time, a point in time after a predetermined period of time from the current point in time, and a point in time at which the user is located in a predetermined area. In addition, the predetermined stimulus corresponds to a stimulus pattern selected by the user of the terminal 130. The stimulus patter may be selected from one or more stimulus patterns offered in association with the loop 2. The one or more stimulus patterns offered in association with loop 2 are determined based on a diagnosis made by the medical specialist treating the user. For example, at least one first stimulus pattern may be determined based on an intensity of stimulus and a type of chronic disease, condition, or symptom, such as the aforementioned depression and insomnia. The one or more stimulus patterns offered in response to a request input from the user may be changed based on the control information received by the user terminal 130 from the electronic device 150.

The user terminal 130 transmits the determined control information to the external device 120. The external device 120 determines the stimulus information based on the control information and transmits the stimulus information and power to the internal device 110 at the point in time desired by the user. The internal device 110 operates using the power received from the external device 120 to apply a stimulus to the user corresponding to the received stimulus information.

In loop 3, the internal device 110 senses biometric information of a user suffering from a symptom, a disease, or a condition, for example, dementia. The internal device 110 senses the biometric information of the user each time that the internal device 110 operates using the power received from the external device 120 or periodically senses the biometric information of the user while the internal device 110 is powered. The internal device 110 transmits the sensed biometric information to the external device 120. The external device 120 transmits the biometric information to the user terminal 130. The biometric information is transmitted to the electronic device 150 from the user terminal 130 (either directly via a wired/wireless network or through the server 140). The medical specialist accesses the biometric information received from the user terminal using the electronic device 150. The medical specialist inputs control information to the electronic device 150 to apply a stimulus to the user based on the received biometric information.

The electronic device 150 transmits the control information to the user terminal 130 (either directly via a wired/wireless network or through the server 140). The user terminal 130 transmits the control information to the external device 120. The external device 120 determines stimulus information based on the control information and wirelessly transmits the determined stimulus information and power to the internal device 110. The internal device 110 operates using the wirelessly transmitted power to generate a stimulus corresponding to the stimulus information and applies the generated stimulus to the user.

The control information input by the medical specialist to the electronic device 150 includes at least one of information on a stimulus pattern that is generated from the biometric information that is received in real time from the internal device and information about a stimulus pattern selected by the medical specialist from at least one second stimulus pattern determined in association with the loop 3. For example, the at least one second stimulus pattern includes a stimulus pattern prescribed by the medical specialist for a condition of the user. The at least one second stimulus pattern includes various stimulus patterns that differ from the at least one first stimulus pattern selected by the user.

The information on the stimulus pattern that is generated based on the real time biometric information includes information configured to reset the stimulus information determined by the external device 120 based on the biometric information received from the user in the loop 1. For example, the medical specialist may determine that an effect of a currently set stimulus is insufficient due to a change in body of the user and desire to increase the intensity of stimulus. In this example, the medical specialist changes the stimulus corresponding to the loop 1 by inputting the information on the stimulus pattern that is generated based on the real time biometric information as the control information.

As a result, a medical specialist is able to provide immediate diagnosis and prescription based on real time data and biometric information reflecting the current state of the user. In addition, a medical special and user may better manage treatment and facilitate care of the user.

Figure 3:
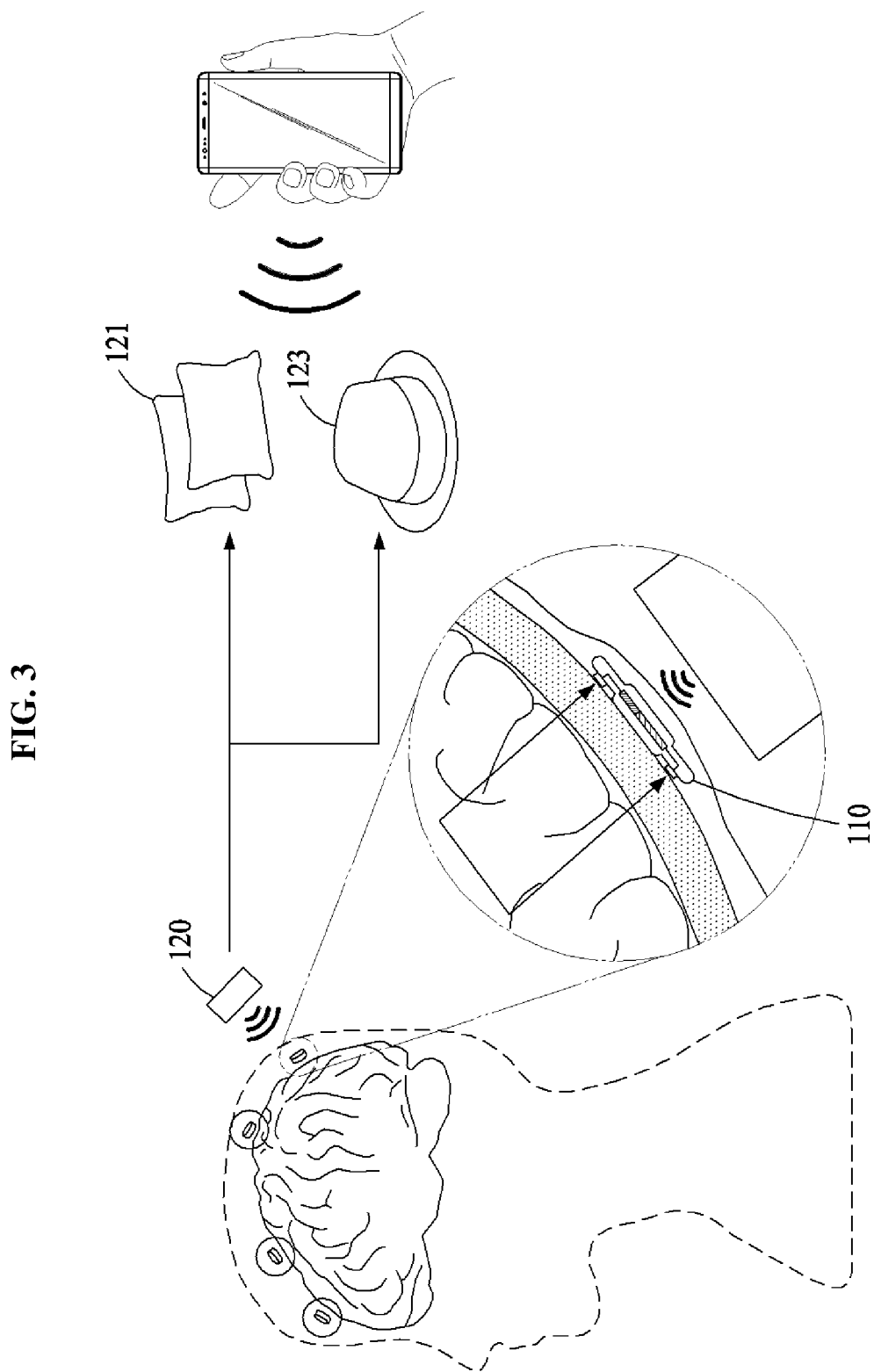
FIG. 3 illustrates an example of an arrangement of an internal device, an external device, and a user terminal.

FIG. 3 illustrates an example of an arrangement of an internal device, an external device, and a user terminal.

The internal device 110 may be provided as a plurality of internal devices or a single internal device that is inserted into the body of a user. In one example, when a single internal device 110 is inserted, the internal device 110 applies a stimulus to various positions through a plurality of electrodes arranged at different positions in the body of the user. The stimulus information transmitted from the external device 120 to the internal device 110 includes information about a pattern of a stimulus to be applied to the user including any electrode that outputs the stimulus. For example, the stimulus information includes information indicating that a stimulus having a predetermined pattern is output from a first electrode and a third electrode.

In another example, when a plurality of internal devices 110 are inserted, each of the plurality of internal devices is arranged at a different position in the body of the user and includes at least one electrode. Stimulus information transmitted from the external device 120 to the plurality of internal devices includes a pattern of a stimulus to be applied to the user, information about which internal device outputs the stimulus, and information about one or more electrodes included in the internal device. For example, the stimulus information includes information indicating that a stimulus having a predetermined pattern is to be output from a second electrode and a fourth electrode. The stimulus information also may specify an intensity and duration of the stimulus that is applied to the user.

The following description will be based on an example in which the internal device 110 is implemented as a single internal device; however, as explained above, the number of internal devices is not limited to this example.

As shown in FIG. 3, the external device 120 located outside the body of the user receives biometric information from the internal device 110 and transmits stimulus information and power to the internal device 110. In one example, the external device 120 is provided as a pillow 121, a hat 123, a helmet (not shown), and the like, which covers, supports, contacts, or is otherwise positioned or located adjacent to the head of the user such that the user receives the stimulus in a daily life.

Figure 4:
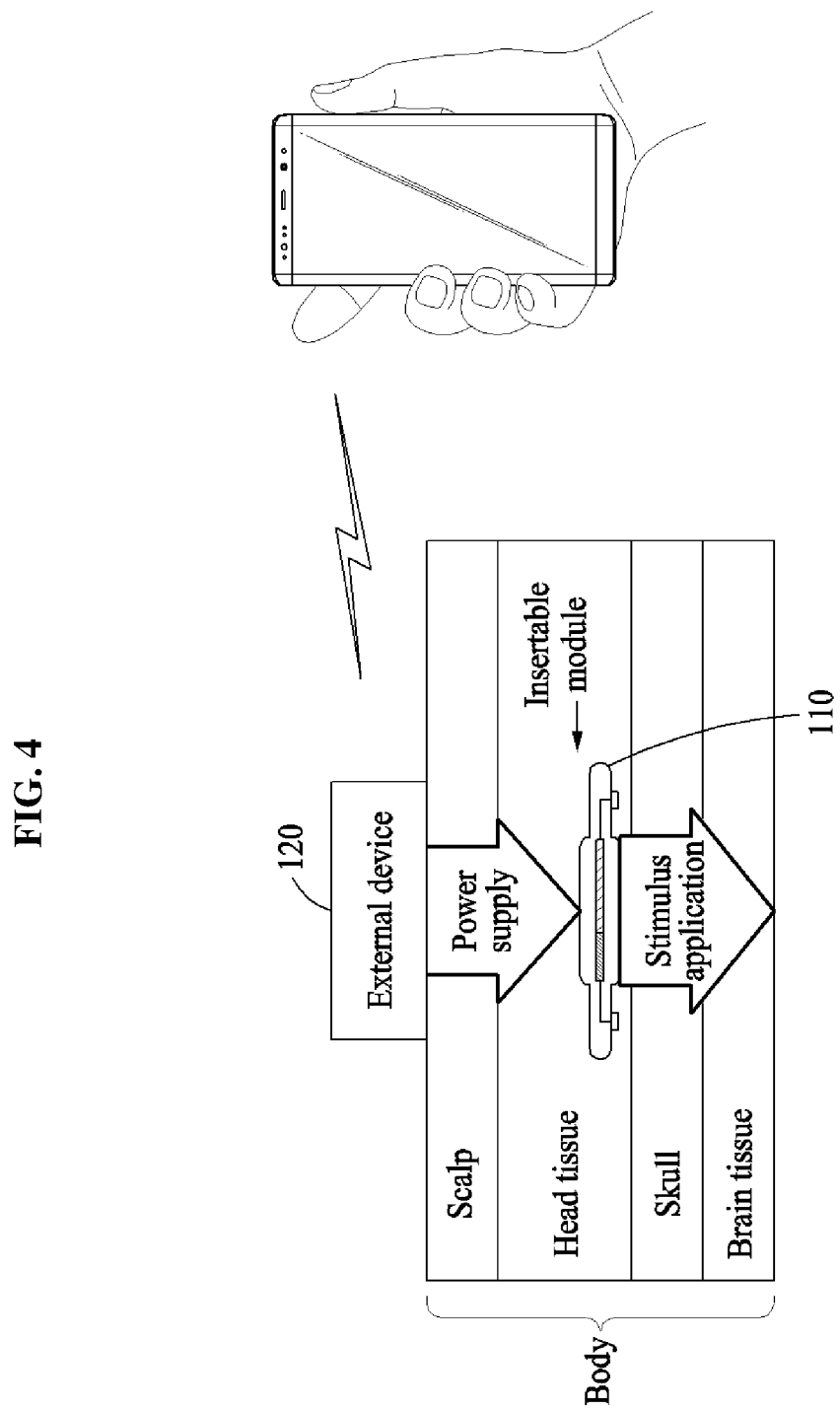
FIG. 4 illustrates an example of the positioning of an internal device that is inserted in a body of a user.

FIG. 4 illustrates an example of a position at which an internal device is inserted in the body of a user. As shown in FIG. 4, the body includes a scalp, head tissue, a skull, and brain tissue. The scalp is formed on the head tissue, and the head tissue covers the skull. The skull protects the brain tissue inside the skull.

As shown in FIG. 4, the internal device 110 is located between the skull and the scalp in the body of a user. For example, the internal device 110 is located in the head tissue that is external and adjacent to the skull. The internal device 110 does not damage the skull when inserted into the body of the user, thereby significantly reducing any surgical burden on the user.

The internal device 110 receives the power from the external device 120 through the electromagnetic induction phenomenon. The internal device 110 is positioned to apply a stimulus generated by the internal device towards the brain tissue.

Figure 5:
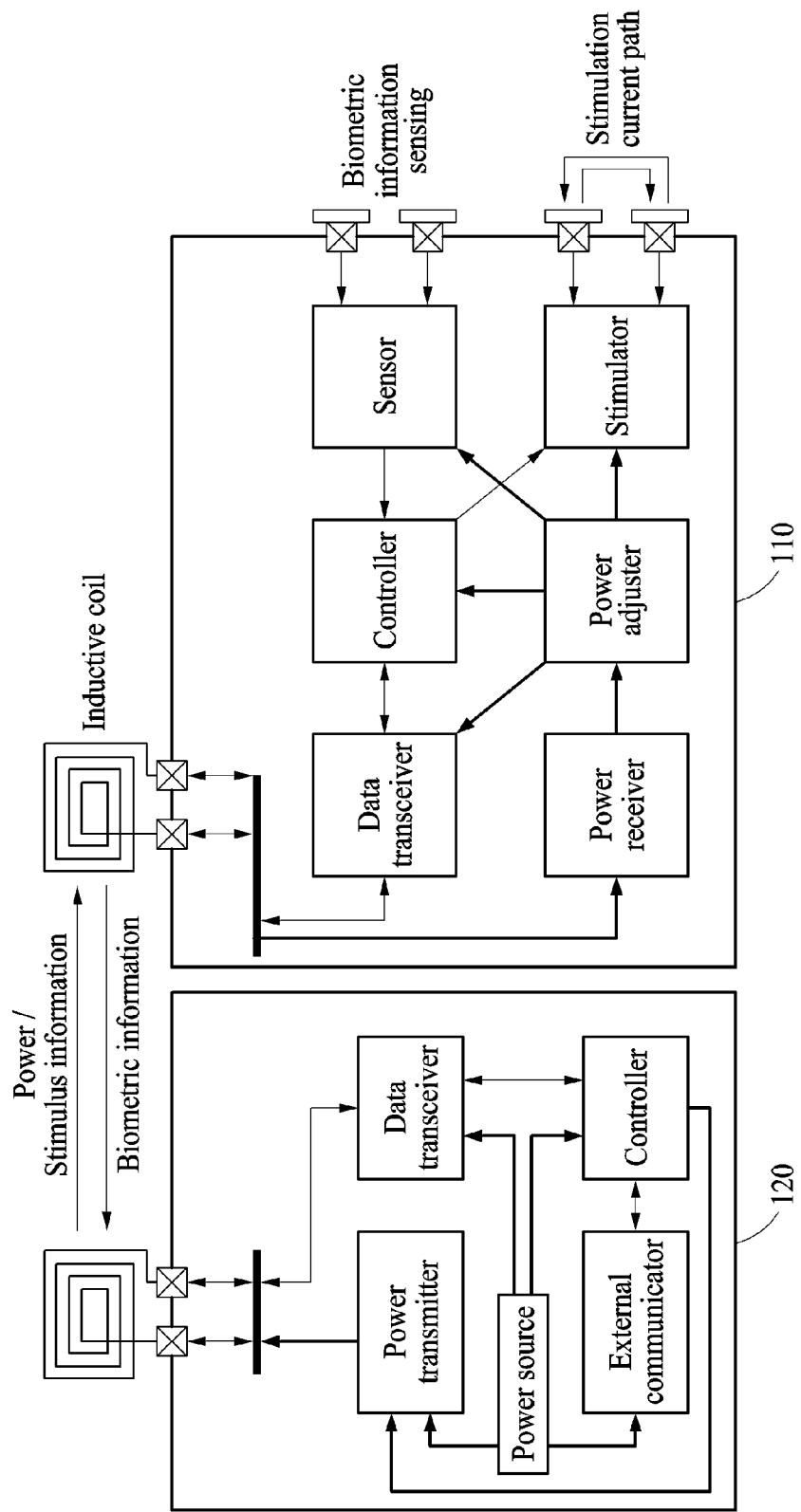
FIG. 5 illustrates an example of the operation of an internal device and an external device.

FIG. 5 illustrates an example of the operation of an internal device and an external device.

As shown in FIG. 5, the internal device 110 includes a data transceiver, a controller, a sensor, a power receiver, a power adjuster, and a stimulator. The internal device 110 receives power that is wirelessly transmitted from the external device 120 via an inductive coil coupled to the power receiver. The power received by the power receiver is transferred to the power adjuster, which provides power to each of the other elements of the internal device 110. While receiving the power wirelessly transmitted from the external device 120, the sensor senses biometric information and provides the sensed biometric to the data transceiver via the controller. The data transceiver transmits the biometric information to the external device 120 through the inductive coil.

As shown in FIG. 5, the external device 120 includes a data transceiver, a power transmitter, a controller, a power source, and an external communicator. Elements of the external device 120 operate based on power supplied from the power source. The external device 120 receives the biometric information transmitted from the internal device 110 via an inductive coil. The inductive coil is coupled to the data transceiver which communicates the received biometric information to the controller. The controller determines whether a stimulus should be applied to the user based on the received biometric information. When it is determined that the stimulus should be applied, based on the biometric information, the controller causes power and stimulus information to be transmitted to the internal device 110. For example, the stimulus information is transmitted from the data transceiver through the inductive coil of the external device 120 to the internal device 110. The power is transmitted from the power transmitter through the inductive coil to the internal device 110. The external communicator included in the external device 120 is used to communicate with a user terminal, as described in greater detail below.

The internal device 110 receives the power transmitted from the external device 120, using the power receiver through the inductive coil. The internal device 110 receives the stimulus information using the data transceiver through the inductive coil. The received stimulus information is transferred to the stimulator through the controller. A stimulus is generated in the stimulator based on the stimulus information and applied to the user.

The internal device 110 operates by receiving the power wirelessly transferred from the external device 120 based on the electromagnetic induction phenomenon instead of using an internal power source, such as a battery. Therefore, the internal device may be permanently inserted into a user without need of change of battery.

Figure 6:
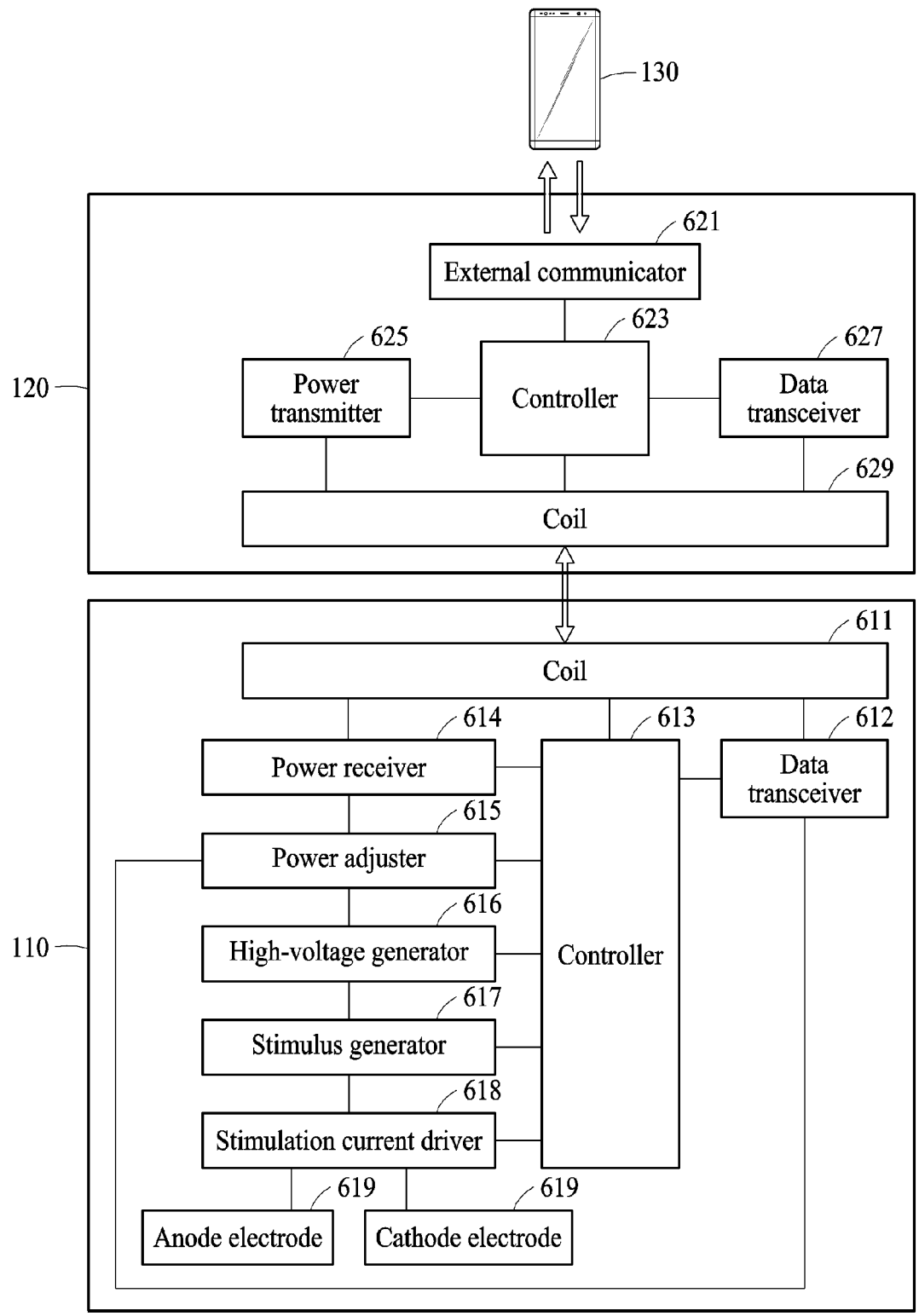
FIG. 6 illustrates an example of the operation of an internal device, an external device, and a user terminal.

FIG. 6 illustrates an example of an operation of an internal device, an external device, and a user terminal.

The internal device 110 includes a coil 611 configured to operate as an antenna, a data transceiver 612 configured to communicate with the external device 120, a controller 613 including a micro controller unit (MCU) (not shown), a power receiver 614 configured to receive power wirelessly transmitted from the external device 120, a power adjuster 615 configured to stably supply the received power to each element of the internal device 110 through a rectifier (not shown), a high-voltage generator 616 configured to generate a high voltage sufficient for stimulus generation, a stimulus generator 617 configured to generate a stimulus based on stimulus information using a pulse generator (not shown), a stimulation current driver 618 configured to drive a stimulation current based on the generated stimulus, an anode electrode 619 and a cathode electrode 620 included in an electrode pair to output the stimulus to a user. The high-voltage generator 616 generates the high voltage and provides the high voltage to the stimulus generator 617. The stimulus generator 617 is configured to provide the stimulation current driver 618 with the high voltage required for stimulus generation.

The external device 120 includes an external communicator 621 configured to communicate with the user terminal 130, a controller 623, a power transmitter 625 configured to wirelessly transmit power to the internal device 110, a data transceiver 627 configured to communicate with the internal device 110, and a coil 629 configured to operate as an antenna for wireless power transmission, data transmission, and data reception. In one example, the external communicator 621 is a device that performs a short-range wireless communication. For example, the external communicator 621 uses infrared communication and/or radio frequency (RF) communication, such as wireless fidelity (Wi-Fi), Bluetooth, Zigbee, and the like.

The coil 629 of the external device 120 wirelessly transmits power and data to the coil 611 of the internal device 110 through magnetic induction.

Figure 7:
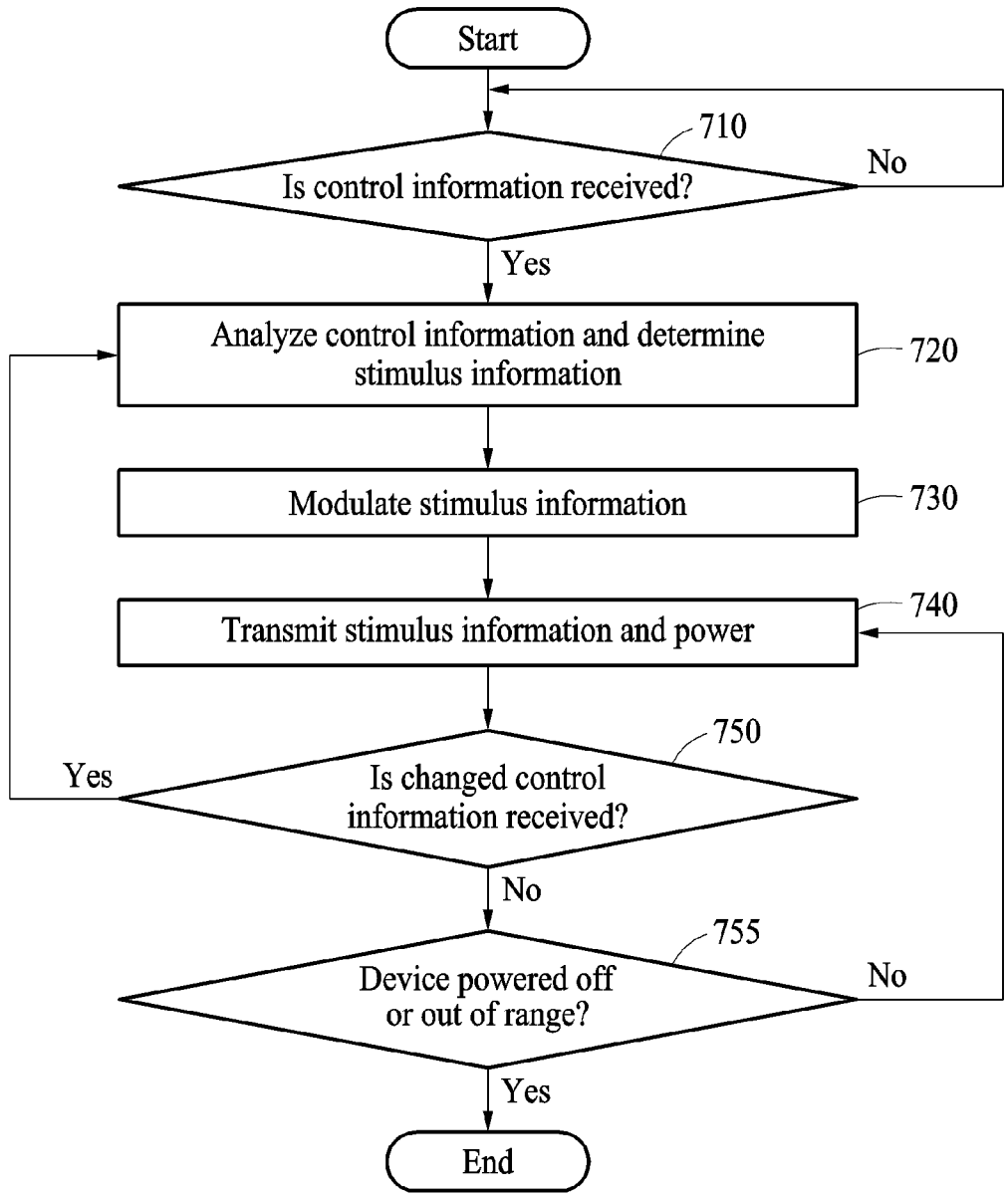
FIG. 7 illustrates an example of the operation of an external device.

FIG. 7 illustrates an example of an operation of an external device 120.

In operation 710, an external device determines whether control information is received from a user terminal. When the control information is not received, the external device continues to wait until it is determined that the control information is received from the user terminal.

When the control information is received, in operation 720, the external device analyzes the received control information to determine stimulus information corresponding to a stimulus to be applied to a user. In operation 730, the external device modulates the stimulus information for wireless communication to the internal device. In operation 740, the external device wirelessly transmits the modulated stimulus information and power to the internal device. In operation 740, the external device continuously performs the wireless power transmission in an amount appropriate for the internal device to apply the desired stimulus to the user after the stimulus information is transmitted to the internal device.

In operation 750, the external device determines whether any changed control information is received from a user terminal. When the changed control information is not received, the external device determines whether the device is powered off or out of range of the internal device in operation 755. If not, the device continuously performs operation 740 as directed by the stimulus information. If so, the operation stops. For example, when the user desires to suspend a stimulus application, the user may turn off the external device or increase a distance between the external device and the internal device, thereby suspending operation between the external device and the internal device.

When the changed control information is received in operation 750, the devices executes operation 720, and the external device analyzes the changed control information and determines the stimulus information based on the new control information. The external device then performs operations 730 and 740 based on the newly received control information and continues to determine whether any changes are made to the control information in operation 750.

Figure 8:
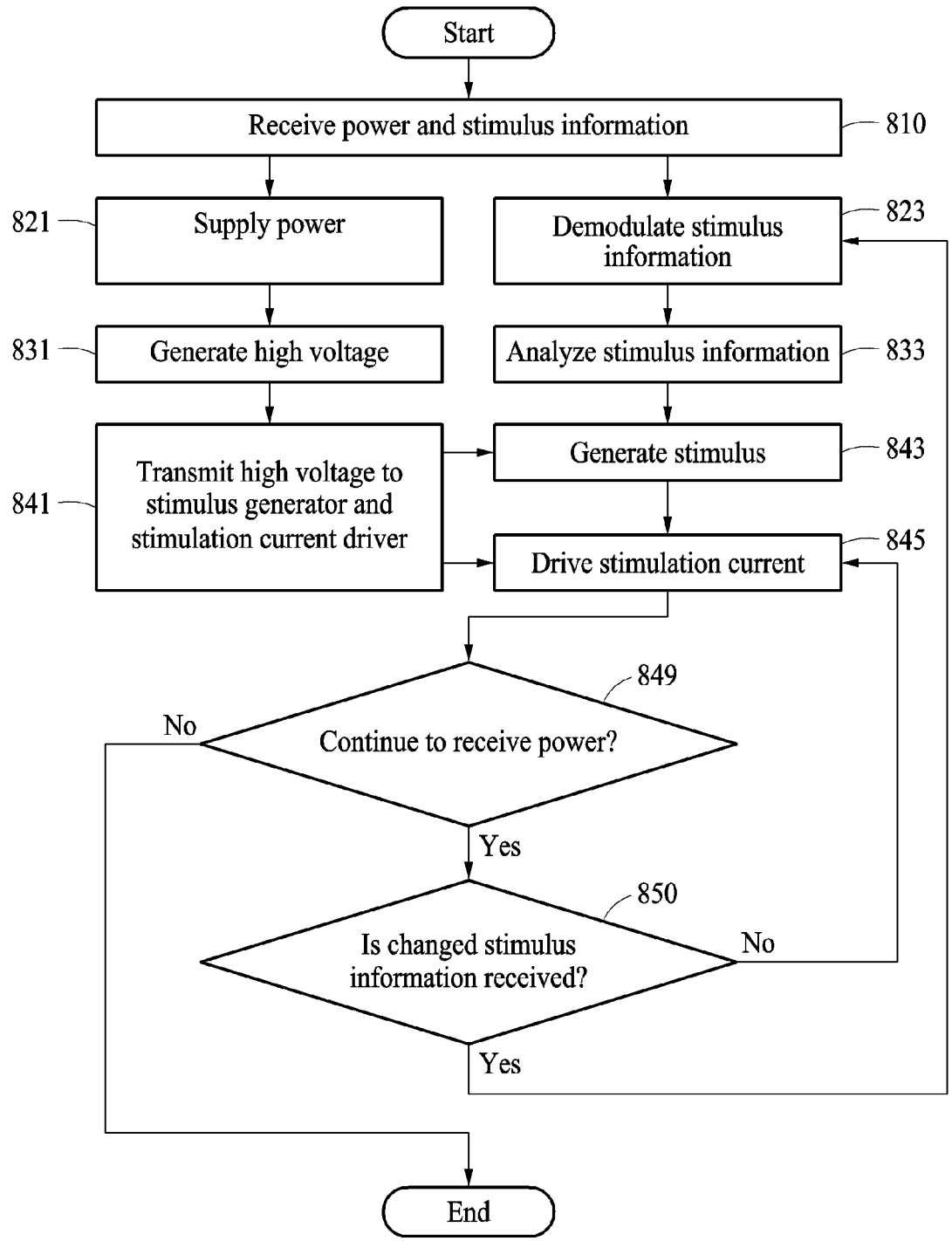
FIG. 8 illustrates an example of the operation of an internal device.

FIG. 8 illustrates an example of an operation of an internal device 110.

In operation 810, an internal device receives power and stimulus information from an external device. In response to the power being received from the external device, the internal device is powered on to receive the stimulus information from the external device.

In operation 821, the internal device supplies power to each element of the internal device through a power adjuster. In operation 831, the internal device generates a high voltage using a high-voltage generator. In operation 841, the internal device transmits the high voltage to a stimulus generator and a stimulation current driver.

In parallel to operations 821 and 831, the internal device performs operations 823 and 833. In operation 823, the internal device demodulates the received stimulus information. In operation 833, the internal device analyzes the demodulated stimulus information. In operation 843, the internal device generates a stimulus based on the stimulus information using the stimulus generator. In operation 845, the internal device drives a stimulation current using the stimulation current driver and applies the stimulus to a user.

In operation 849, if the device continues to have power transmitted the operation continues to operation 850. If not, the operation ends.

In operation 850, the internal device monitors whether changed stimulus information is received from the external device while the stimulus is applied. When the changed stimulus information is not received, the internal device continuously performs operation 845 to drive the stimulation current while the power is supplied.

However, when the changed stimulus information is received, the internal device performs operations 810, 823, 833, 843, and 845 based on the changed stimulus information.

The internal device is turned off when the power supplied from the external device is suspended.

Figure 9:
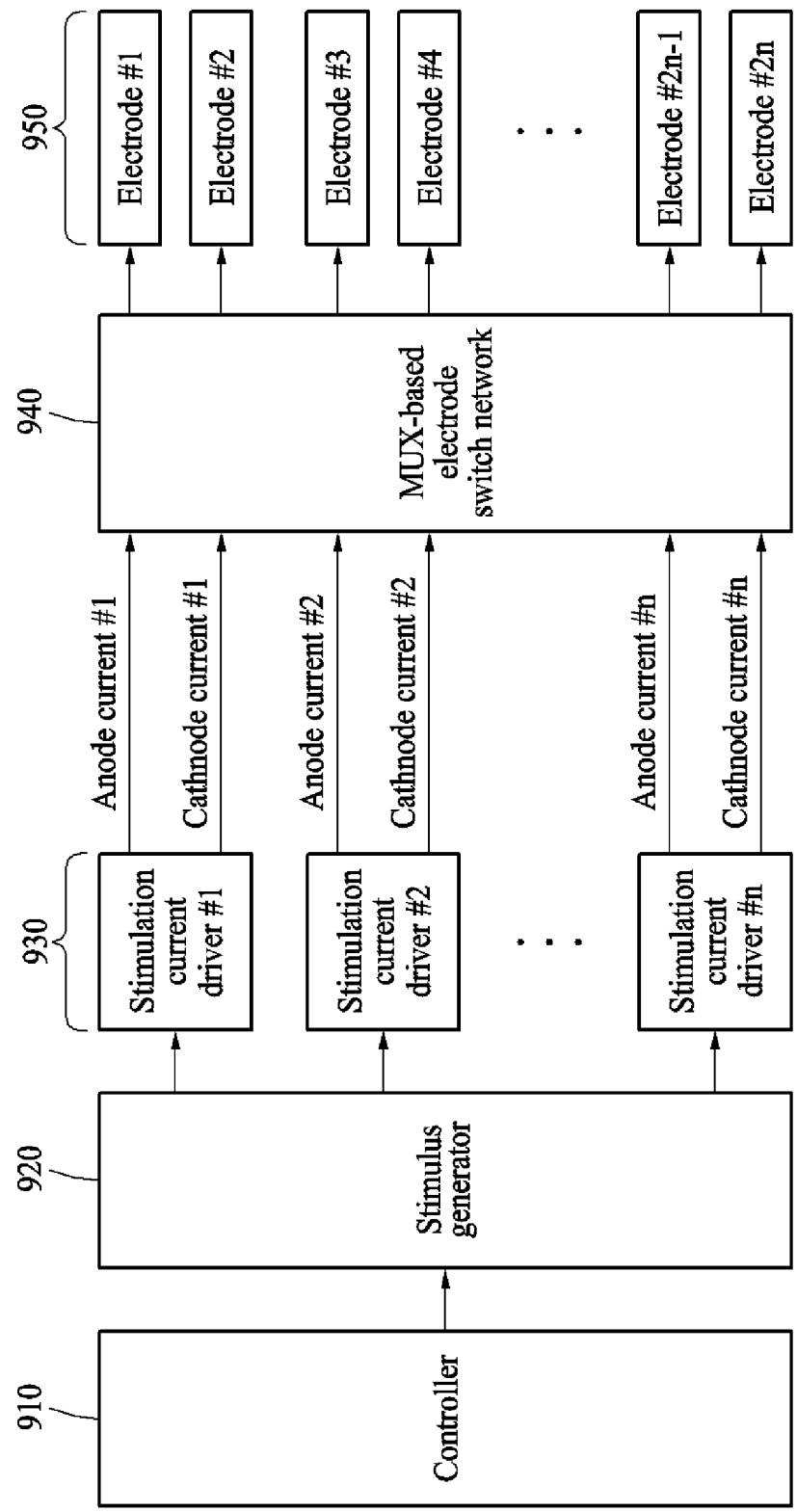
FIG. 9 illustrates an example of an internal device outputting a stimulus through a plurality of electrodes.

FIG. 9 illustrates an example of an internal device outputting a stimulus through a plurality of electrodes.

A controller 910 controls a stimulus generator 920 based on stimulus information received from an external device. The stimulus generator 920 generates a stimulus based on the stimulus information in response to controller 910 to drive stimulation current drivers 930 through a number of channels corresponding to each current driver 930. For example, the number of the stimulation current drivers 930 may correspond to a number of channels for stimulation. Each of the stimulation current drivers 930 generates an anode current and a cathode current for each of the channels corresponding to a pair of electrodes 950 determined by a multiplexer (MUX)-based electrode switch network 940.

An anode electrode and a cathode electrode included in the electrode pair are dynamically changed based on a stimulus received through the MUX-based electrode switch network 940.

Figure 10:
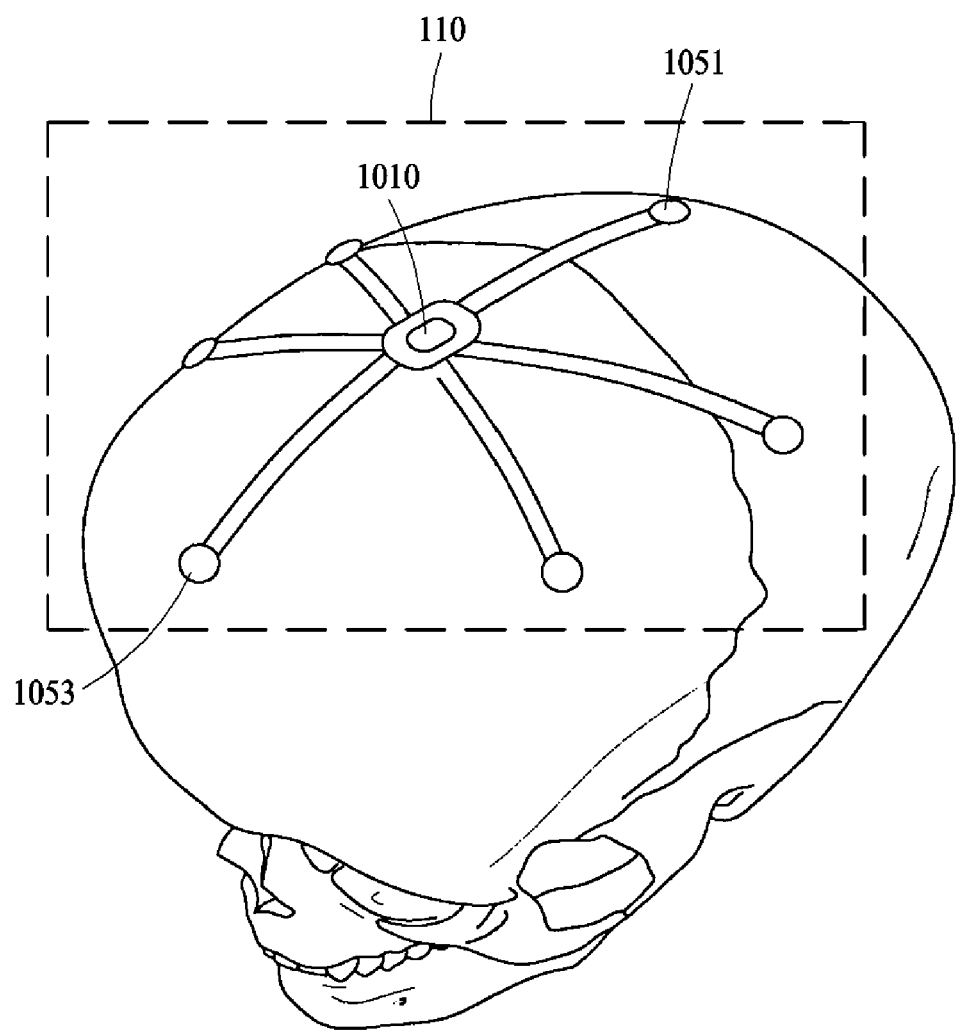
FIGS. 10 and 11 illustrate examples of a plurality of electrodes arranged in the head of a user.
Figure 11:
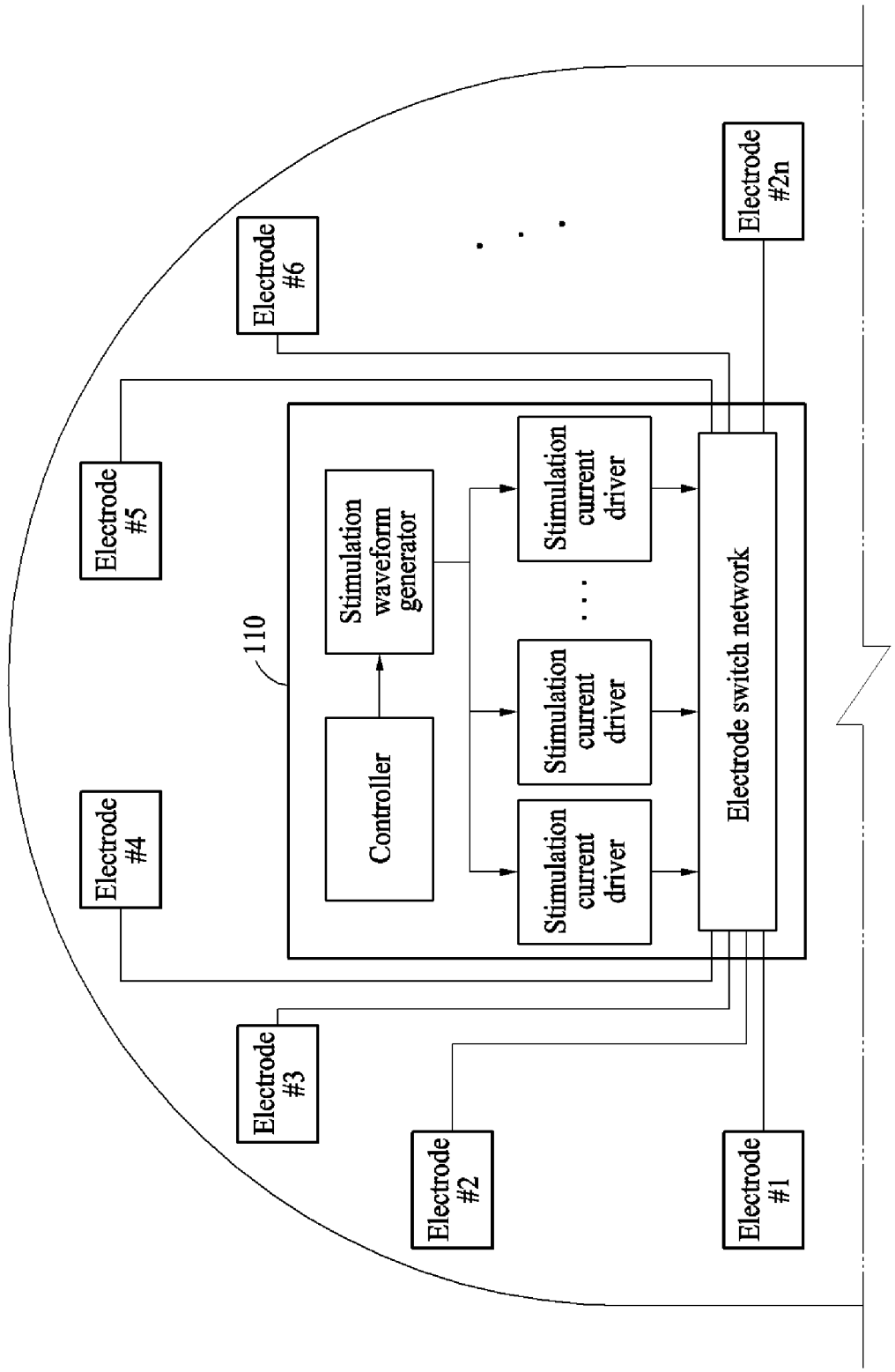

FIGS. 10 and 11 illustrate example of the arrangement of a plurality of electrodes on the head of a user.

As shown in FIG. 10, the internal device 110 is located external to a skull of a user. A controller 1010 is physically and directly connected to each of a plurality of electrodes. For example, the controller and electrodes may be connected via one or more of a printed circuit board (PCB), a flexible printed circuit board (FPCB), and a wire. The connection between the controller 1010 and the plurality of electrodes is coated with a biocompatible material to prevent a leakage of the stimulus and protect the living tissue of the user. In one example, the portion of the device 110 in contact with the living tissue to which the stimulus is applied may be coated with, for example, platinum. As shown in FIG. 10, separate connector connects the controller 1010 to each of the plurality of electrodes. In this example, conductive portions of the plurality of electrodes and the controller 1010 are physically connected using a fixing member.

In this example, a coil included in the internal device is located adjacent to a scalp of the user to facilitate reception of power and stimulus information from the external device. The plurality of electrodes is arranged adjacent to the skull to easily apply the stimulus to the user.

The plurality of electrodes of the internal device include at least one anode electrode 1051 and cathode electrode 1053 pair. As illustrated in FIG. 10, the anode electrode 1051 and the cathode electrode 1053 are arranged to be radially symmetric with respect to the controller 1010. However, embodiments are not limited to such an arrangement.

The number of the plurality of electrodes is at least twice a number of channels through which the stimulus is applied from the controller 1010. An anode electrode and a cathode electrode are changed based on the stimulus applied from the controller 1010. For example, a portion of the plurality of electrodes may operate in response to the stimulus being applied. Also, an anode electrode and a cathode electrode included in an electrode pair may be dynamically changed in response to the stimulus being applied. Electrodes receiving a stimulus may also be dynamically changed based on a stimulation train or a stimulation area as further discussed with reference to FIG. 14.

Since a plurality of channels is independently operated, a stimulus pattern may be applied to the user in a wide range by choosing various connections of the plurality of channels. For example, a plurality of channels is spread over the entire head of the user such that a plurality of electrodes corresponding to stimulation points sequentially outputs a stimulus or an intensity of stimulus is gradually adjusted toward a predetermined electrode. As such, a stimulus is applied to the entire head of the user. For example, the stimulus is effectively applied to the entire brain including a frontal lobe, a temporal lobe, and a parietal lobe of the user.

Figure 12:
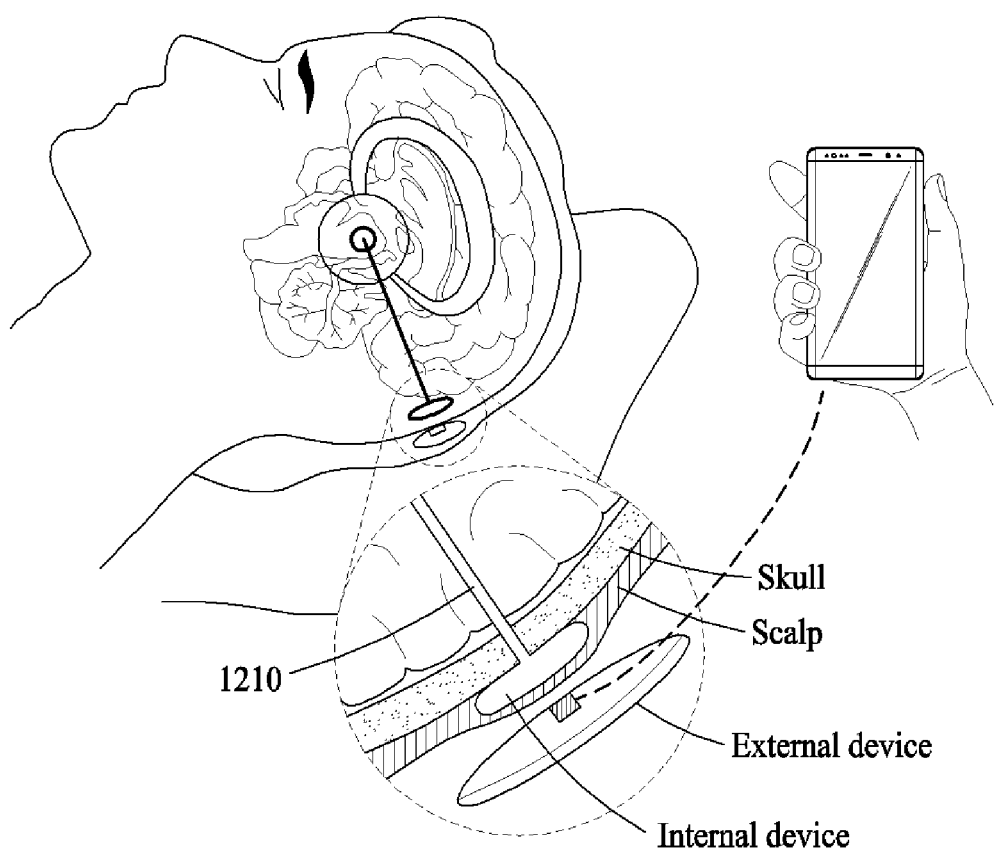
FIGS. 12 and 13 illustrate examples of an electrode applied to an internal device.
Figure 13:
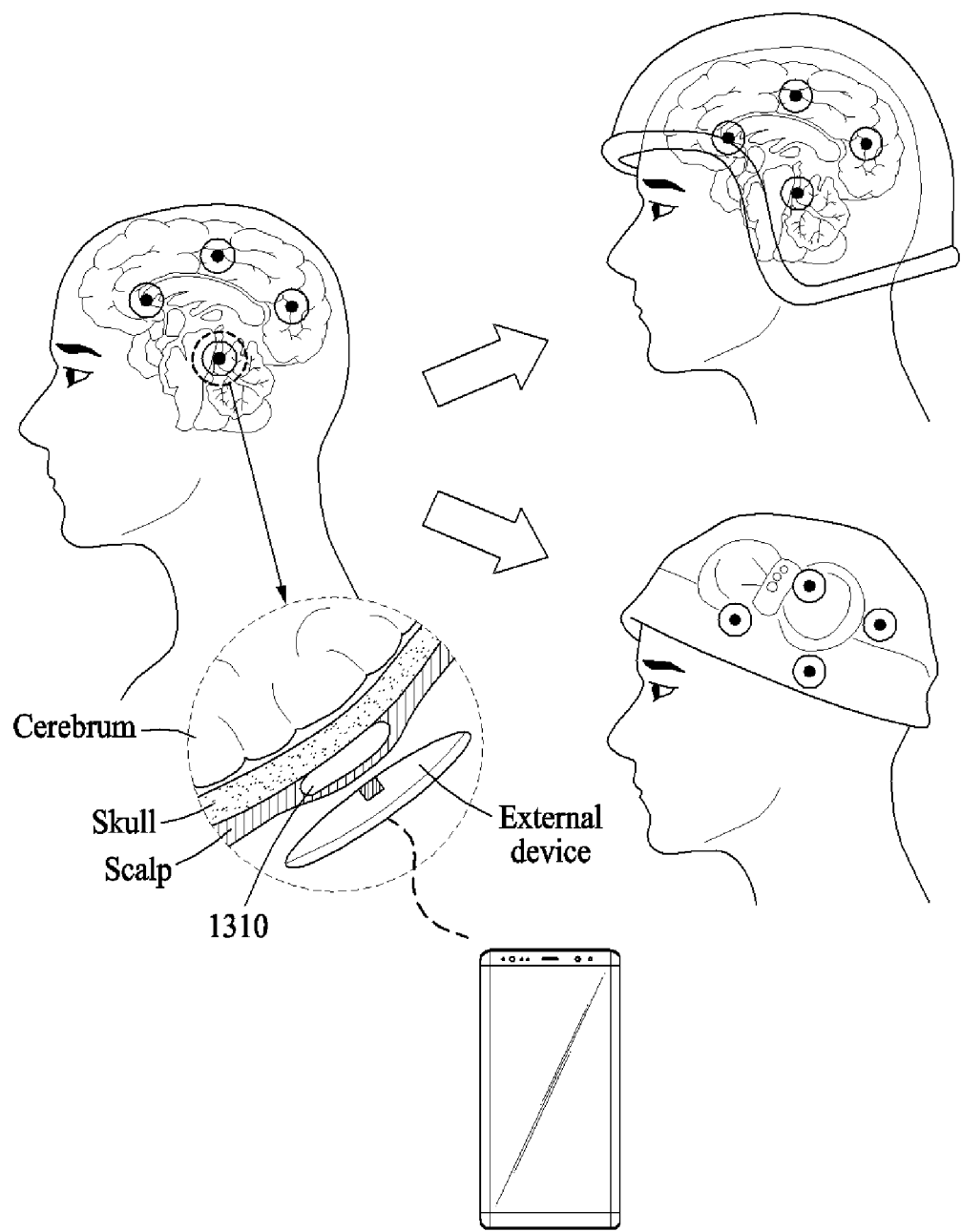

FIGS. 12 and 13 illustrate examples of how a stimulus of an electrode of an internal device is applied to a user.

Referring to FIG. 12, an internal device applies a stimulus to a user based on a deep brain stimulation (DBS) scheme. As shown in FIG. 12, the internal device includes a lead 1210. The lead 1210 is inserted to the brain cortex of the user. The internal device applies the stimulus using the lead 1210 to stimulate a deep brain part. In this example, elements of the internal device other than the lead 1210 are located externally to the skull. A hole is formed in the skull in which the lead 1210 is passed through to reach the cortex.

Referring to FIG. 13, an internal device applies a stimulus to a user based on a transcranial direct current stimulation (tDCS) scheme. Unlike the example shown in FIG. 12, an invasion hole in the skull of the user is not necessary. In this example, an electrode 1310 of the internal device applies the stimulus from an outside of the skull. As illustrated in FIG. 13, the external device that transmits power and stimulus information is provided in a helmet or a hat. With such a configuration, the user is able to comfortably receive the stimulus and easily control of the stimulus applied time or intensity while going about their daily life.

Figure 14:
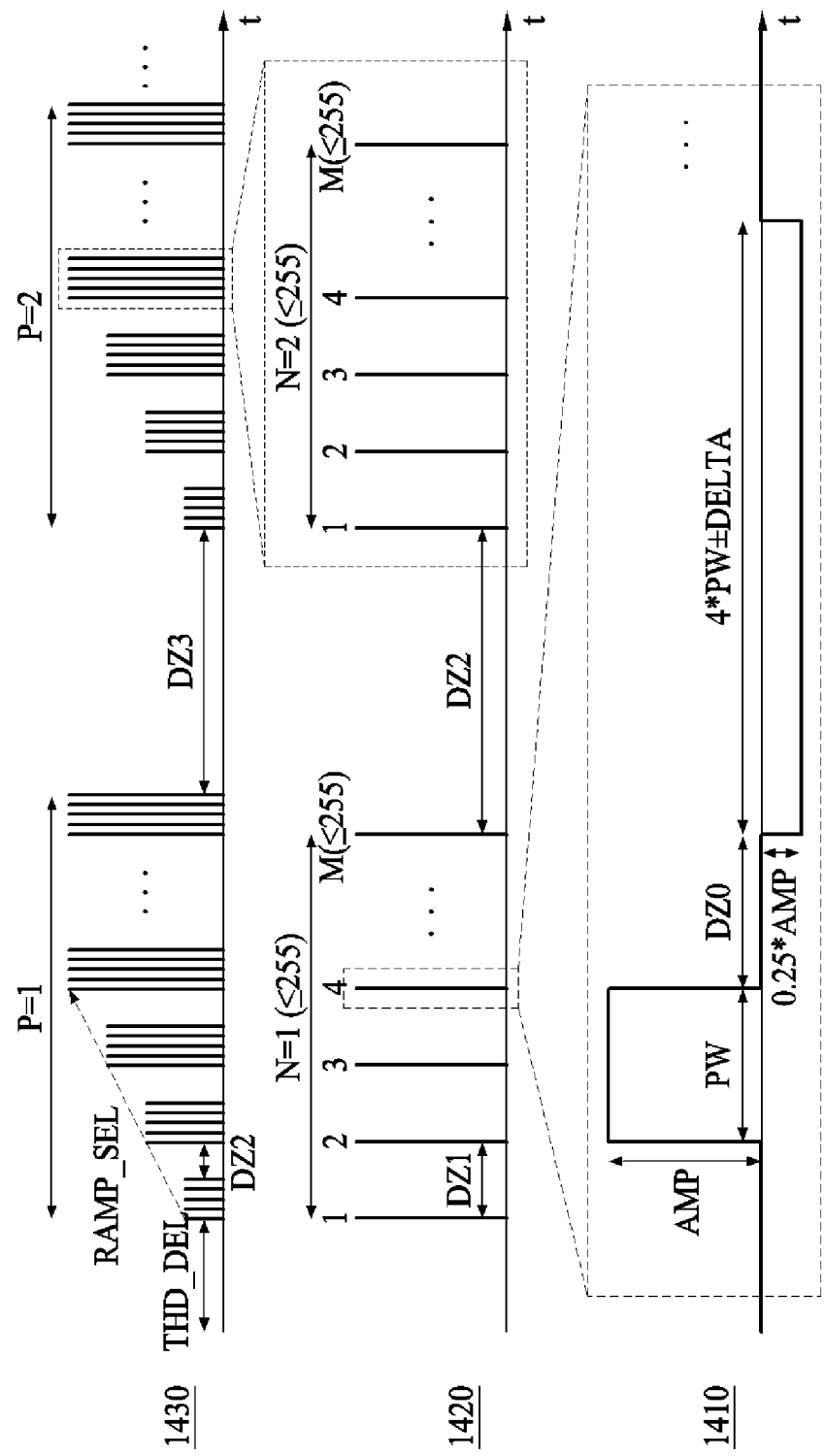
FIG. 14 illustrates an example of a stimulus applied to a user.

FIG. 14 illustrates an example of a stimulus applied to a user.

A stimulus is separated into a stimulation pair 1410, a stimulation train 1420, and a stimulation area 1430.

As shown in FIG. 14, the stimulation pair 1410 includes two stimulation pulses. The stimulation pair 1410 is determined based on an amplitude AMP and a pulse width PW of a stimulation pulse, and an interval, for example, a dead zone DZ0 between the two stimulation pulses. The amplitude AMP indicates an intensity of stimulation, and the pulse width PW indicates a duration of the stimulation. When the stimulus is only applied in one direction to a tissue, the tissue may become necrotic. Thus, the stimulus may need to be applied in another direction thereafter. The two stimulation pulses configure the stimulation pair 1410.

The stimulation train 1420 includes a plurality of stimulation pairs. The stimulation train 1420 is determined based on an interval DZ1 between stimulation pairs, a number M of consecutive stimulation pairs, an interval DZ2 between stimulation trains, and a number N of stimulation trains.

The stimulation area 1430 includes a plurality of stimulation trains. The stimulation area 1430 is determined based on an initial delay THD_DEL, a degree RAMP_SEL to which the intensity of stimulus increases, the number of consecutive stimulation trains, and an interval DZ3 of stimulation areas.

The stimulus applied to the user includes a plurality of stimulation areas. Also, stimulus information includes parameters, such as the stimulation pair 1410, the stimulation train 1420, and the stimulation area 1430, as illustrated in FIG. 14.

FIG. 15 illustrates an example of a stimulation interface.

A user or a medical specialist intuitively adjusts a stimulus to be applied to the user through a stimulation interface as illustrated in FIG. 15. The stimulation interface is provided to the user or the medical specialist through a program or an application installed in a user terminal or an electronic device. The stimulation interface is used to adjust the stimulus to be applied for each group or unit, monitor stimulus information and a state of connection between an internal device and an external device in real time, and verify a predicted stimulation termination time.

Figure 16:
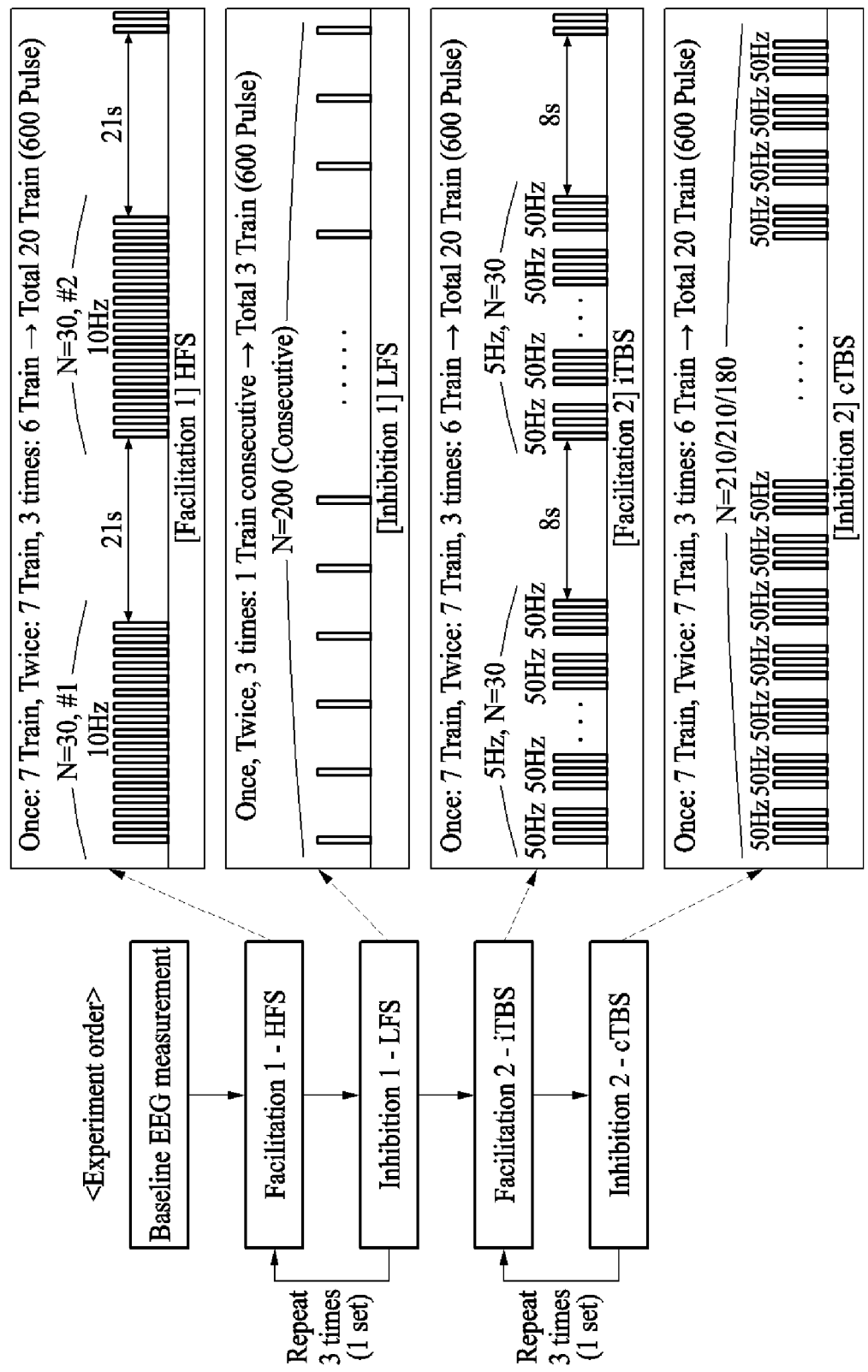
FIG. 16 illustrates an example of a stimulus applied to a user.

FIG. 16 illustrates an example of a stimulus applied to a user.

A baseline EEG is measured. Based on a result of the measuring, a facilitation 1 stimulus corresponding to high-frequency stimulation (HFS) and an inhibition 1 stimulus corresponding to low-frequency stimulation (LFS) are repetitively applied. Thereafter, a facilitation 2 stimulus corresponding to intermittent theta burst stimulation (iTBS) and an inhibition 2 stimulus corresponding to continuous theta burst stimulation (cTBS) are repetitively applied. The stimuli illustrated in FIG. 16 are merely one example of stimuli and thus do not limit the type or kind of stimulus to be applied to a user.

Figure 17:
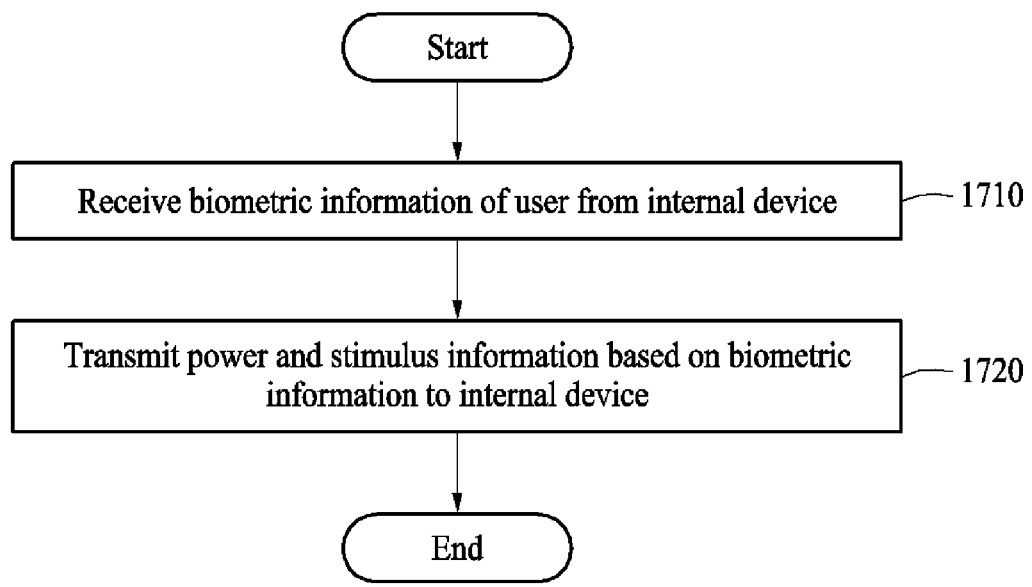
FIG. 17 illustrates an example of the operation of an external device.

FIG. 17 illustrates an example of an operation of an external device.

Referring to FIG. 17, in a method of operating an external device, the external device receives biometric information of a user from an internal device inserted in the body of the user in operation 1710. In operation 1715, the external device determines the power for driving the internal device and stimulus information for the stimulus to be applied to the user based on the biometric information received from the internal device. In operation 1720, the external device transmits power for driving the internal device and stimulus information to the internal device.

Figure 18:
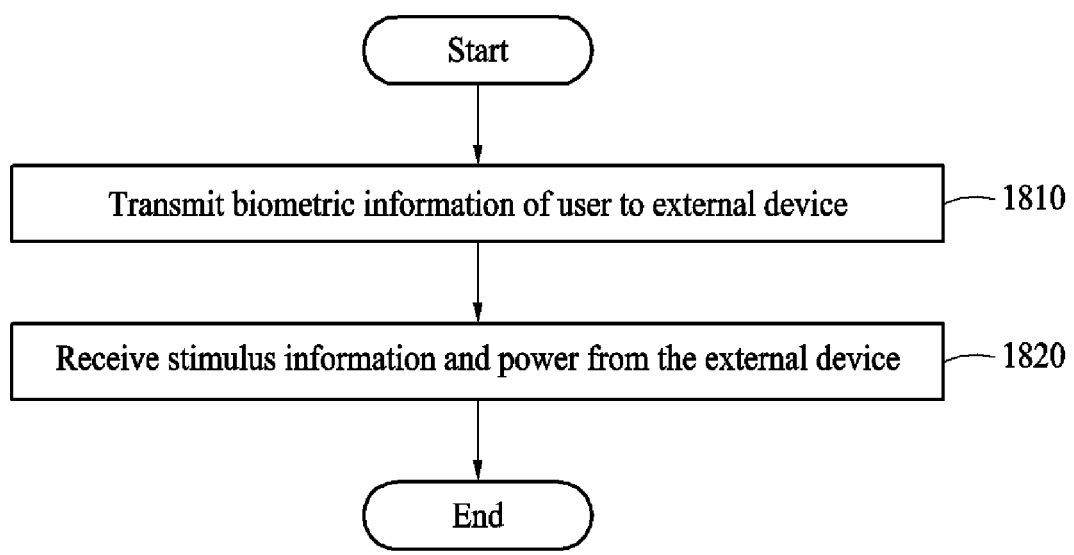
FIG. 18 illustrates an example of the operation of an internal device.

FIG. 18 illustrates an example of an operation of an internal device.

Referring to FIG. 18, in a method of operating an internal device, the internal device transmits biometric information of a user to an external device located outside a body of the user in operation 1810. In operation 1820, the internal device receives, from the external device, stimulus information on a stimulus to be applied to the user and power for driving the internal device. In operation 1830, the internal device applies the stimulus to the user based on the stimulus information.

Figure 19:
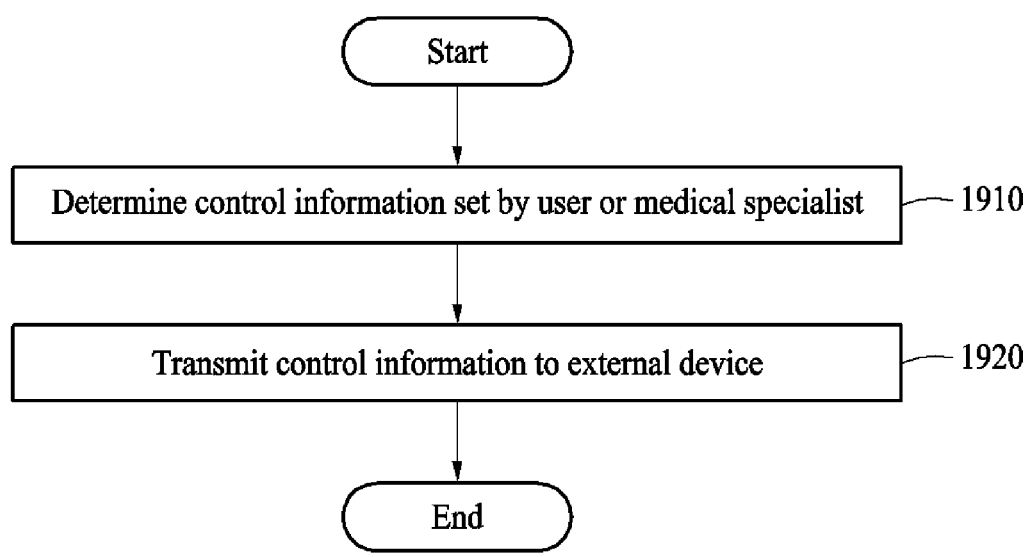
FIG. 19 illustrates an example of the operation of a user terminal.

FIG. 19 illustrates an example of an operation of a user terminal.

Referring to FIG. 19, in a method of operating a user terminal, the user terminal determines control information set by a user or a medical specialist diagnosing the user in operation 1910. In operation 1920, the user terminal transmits the control information to an external device that is located outside a body of the user. The control information is used to determine stimulus information on a stimulus to be applied to the user. The stimulus information and power are transmitted from the external device to an internal device inserted in the body of the user.

Figure 20:
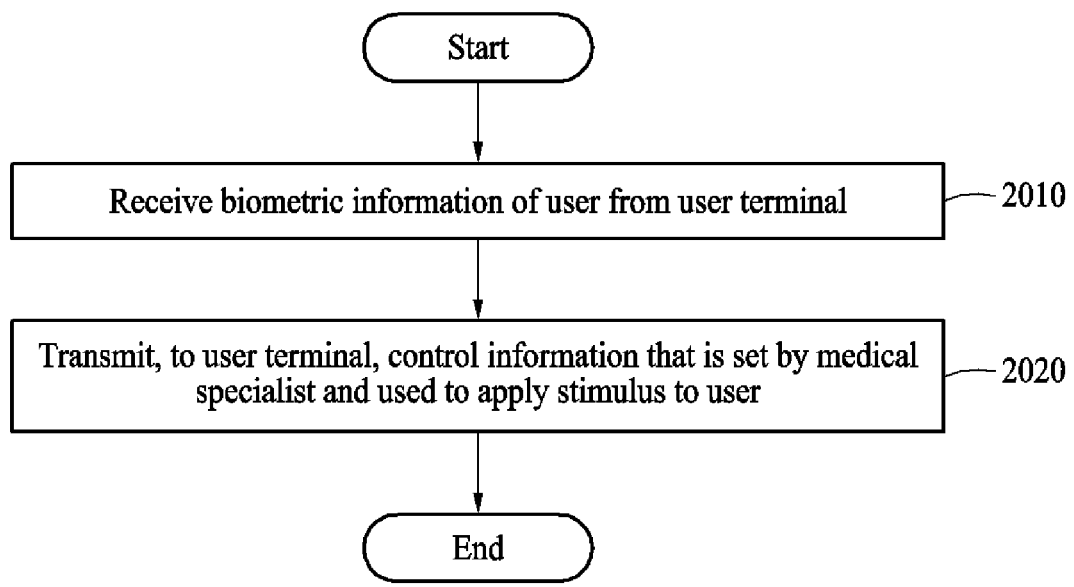
FIG. 20 illustrates an example of the operation of an electronic device.

FIG. 20 illustrates an example of an operation of an electronic device.

As shown in FIG. 20, in operation 2010, the electronic device receives biometric information of a user from a user terminal controlled by the user. The biometric information is sensed by an internal device in the body of the user. In operation 2015, control information based on stimulus information is set by a medical specialist. The stimulus information may be set the medical specialist based on the received biometric information. The control information provides stimulus information on a stimulus to be applied to the user. In operation 2020, the electronic device transmits the control information to the user terminal.

The examples and description of FIGS. 1 through 16 are also applicable to operations provided in FIGS. 17 through 20, and are not repeated for brevity.

Figure 21:
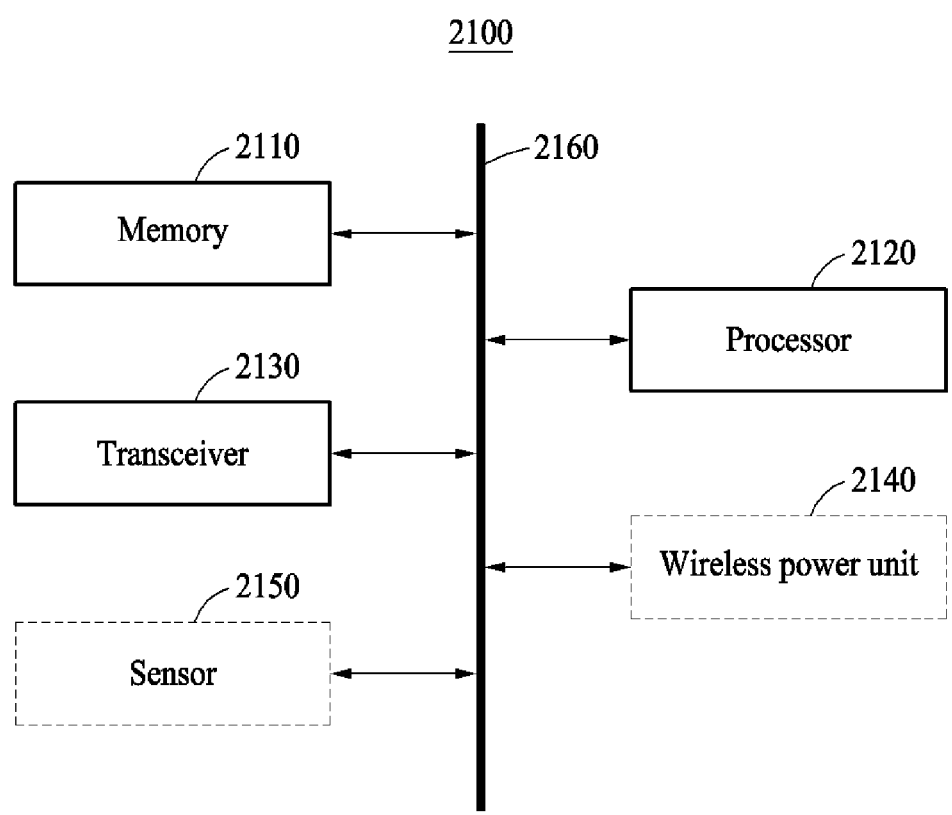
FIG. 21 illustrates an example of an apparatus.

FIG. 21 illustrates an example of an apparatus.

Referring to FIG. 21, an apparatus 2100 includes a memory 2110, a processor 2120, and a transceiver 2130. The apparatus 2100 also may further include in certain embodiments a wireless power unit 2140 and a sensor 2150. The memory 2110, the processor 2120, the transceiver 2130, the wireless power unit 2140, and the sensor 2150 communicate with one another through a bus 2160.

The processor 2120 includes, for example, a device configured to execute instructions or programs, or control an operation of the apparatus 2100. The memory 2110 includes an instruction to be read by the processor 2120. When the instruction stored in the memory 2110 is executed in the processor 2120, the processor 2120 performs an operation described in the foregoing explanation. The memory 2110 is a volatile memory or a non-volatile memory.

When the apparatus 2100 is an external device, the apparatus 2100 includes the memory 2110, the processor 2120, the transceiver 2130, and the wireless power unit 2140. The apparatus 2100 communicates with an internal device or a user terminal through the transceiver 2130 and wirelessly transmits power to the internal device through the wireless power unit 2140.

When the apparatus 2100 is an internal device, the apparatus 2100 includes the memory 2110, the processor 2120, the transceiver 2130, the wireless power unit 2140, and the sensor 2150. The apparatus 2100 communicates with an external device through the transceiver 2130 and wirelessly receives power from the external device through the wireless power unit 2140. Also, the apparatus 2100 senses biometric information of a user using the sensor 2150.

When the apparatus 2100 is implemented as a user terminal, the apparatus 2100 includes the memory 2110, the processor 2120, and the transceiver 2130. The apparatus 2100 communicates with an external device or an electronic device through the transceiver 2130.

When the apparatus 2100 is an electronic device, the apparatus 2100 includes the memory 2110, the processor 2120, and the transceiver 2130. The apparatus 2100 communicates with the user terminal through the transceiver 2130.

The operations described above are also applicable to the various embodiments of the apparatus 2100, and are not repeated for brevity.

The apparatus, units, modules, devices, and other components described herein are implemented by hardware components. Examples of hardware components that may be used to perform the operations described herein where appropriate include controllers, sensors, generators, drivers, memories, comparators, arithmetic logic units, adders, subtractors, multipliers, dividers, integrators, and any other electronic components configured to perform the operations described herein. In other examples, one or more of the hardware components that perform the operations described herein are implemented by computing hardware, for example, by one or more processors or computers. A processor or computer may be implemented by one or more processing elements, such as an array of logic gates, a controller and an arithmetic logic unit, a digital signal processor, a microcomputer, a programmable logic controller, a field-programmable gate array, a programmable logic array, a microprocessor, or any other device or combination of devices that is configured to respond to and execute instructions in a defined manner to achieve a desired result. In one example, a processor or computer includes, or is connected to, one or more memories storing instructions or software that are executed by the processor or computer. Hardware components implemented by a processor or computer may execute instructions or software, such as an operating system (OS) and one or more software applications that run on the OS, to perform the operations described herein. The hardware components may also access, manipulate, process, create, and store data in response to execution of the instructions or software. For simplicity, the singular term "processor" or "computer" may be used in the description of the examples described herein, but in other examples multiple processors or computers may be used, or a processor or computer may include multiple processing elements, or multiple types of processing elements, or both. For example, a single hardware component or two or more hardware components may be implemented by a single processor, or two or more processors, or a processor and a controller. One or more hardware components may be implemented by one or more processors, or a processor and a controller, and one or more other hardware components may be implemented by one or more other processors, or another processor and another controller. One or more processors, or a processor and a controller, may implement a single hardware component, or two or more hardware components. A hardware component may have any one or more of different processing configurations, examples of which include a single processor, independent processors, parallel processors, single-instruction single-data (SISD) multiprocessing, single-instruction multiple-data (SIMD) multiprocessing, multiple-instruction single-data (MISD) multiprocessing, and multiple-instruction multiple-data (MIMD) multiprocessing. The methods that perform the operations described herein are performed by computing hardware, for example, by one or more processors or computers, implemented as described above executing instructions or software to perform the operations. For example, a single operation or two or more operations may be performed by a single processor, or two or more processors, or a processor and a controller. One or more operations may be performed by one or more processors, or a processor and a controller, and one or more other operations may be performed by one or more other processors, or another processor and another controller. One or more processors, or a processor and a controller, may perform a single operation, or two or more operations.

Instructions or software to control a processor or computer to implement the hardware components and perform the methods as described above are written as computer programs, code segments, instructions or any combination thereof, for individually or collectively instructing or configuring the processor or computer to operate as a machine or special-purpose computer to perform the operations performed by the hardware components and the methods as described above. In one example, the instructions or software include machine code that is directly executed by the processor or computer, such as machine code produced by a compiler. In another example, the instructions or software include higher-level code that is executed by the processor or computer using an interpreter. Programmers of ordinary skill in the art can readily write the instructions or software based on the block diagrams and the flow charts illustrated in the drawings and the corresponding descriptions in the specification, which disclose algorithms for performing the operations performed by the hardware components and the methods as described above.

Instructions or software to control computing hardware, for example, one or more processors or computers, to implement the hardware components and perform the methods as described above may be written as computer programs, code segments, instructions or any combination thereof, for individually or collectively instructing or configuring the one or more processors or computers to operate as a machine or special-purpose computer to perform the operations that are performed by the hardware components and the methods as described above. In one example, the instructions or software include machine code that is directly executed by the one or more processors or computers, such as machine code produced by a compiler. In another example, the instructions or software includes higher-level code that is executed by the one or more processors or computer using an interpreter. The instructions or software may be written using any programming language based on the block diagrams and the flow charts illustrated in the drawings and the corresponding descriptions in the specification, which disclose algorithms for performing the operations that are performed by the hardware components and the methods as described above.

The instructions or software to control computing hardware, for example, one or more processors or computers, to implement the hardware components and perform the methods as described above, and any associated data, data files, and data structures, may be recorded, stored, or fixed in or on one or more non-transitory computer-readable storage media. Examples of a non-transitory computer-readable storage medium include read-only memory (ROM), random-access programmable read only memory (PROM), electrically erasable programmable read-only memory (EEPROM), random-access memory (RAM), dynamic random access memory (DRAM), static random access memory (SRAM), flash memory, non-volatile random access memory, CD-ROMs, CD-Rs, CD+Rs, CD-RWs, CD+RWs, DVD-ROMs, DVD-Rs, DVD+Rs, DVD-RWs, DVD+RWs, DVD-RAMs, BD-ROMs, BD-Rs, BD-R LTHs, BD-REs, blue-ray or optical disk storage, hard disk drive (HDD), solid state drive (SSD), flash memory, a card type memory such as multimedia card micro or a card (for example, secure digital (SD) or extreme digital (XD)), magnetic tapes, floppy disks, magneto-optical data storage devices, optical data storage devices, hard disks, solid-state disks, and any other device that is configured to store the instructions or software and any associated data, data files, and data structures in a non-transitory manner and provide the instructions or software and any associated data, data files, and data structures to one or more processors or computers so that the one or more processors or computers can execute the instructions. In one example, the instructions or software and any associated data, data files, and data structures are distributed over network-coupled computer systems so that the instructions and software and any associated data, data files, and data structures are stored, accessed, and executed in a distributed fashion by the one or more processors or computers.

While this disclosure includes specific examples, it will be apparent after an understanding of the disclosure of this application that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner, and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. A medical device method, the method comprising:
   receiving, by an electronic device, biometric information of a user sensed by an internal device in a body of the user from a user terminal controlled by the user;
   determining control information set by a medical specialist controlling the electronic device, the control information being configured to cause an external device that is located outside a body of the user to wirelessly transmit stimulus information and power to the internal device inserted in the body of the user in response to the external device receiving the control information; and
   transmitting the control information to the user terminal,
   wherein the control information includes information used to select a stimulus pattern from at least one stimulus pattern determined in association with a feedback loop including the internal device, the external device, the user terminal, and the electronic device.

2. The method of claim 1, wherein the control information further includes
   information indicating a stimulus pattern generated in real time in response to the received biometric information.

3. A medical device system, the system comprising:
   an electronic device controlled by a medical specialist, the electronic device comprising:
   a data transceiver; and
   a controller configured to cause the data transceiver to receive biometric information of a user sensed by an internal device in a body of the user from a user terminal controlled by the user, to determine control information set by a medical specialist, the control information being configured to cause an external device that is located outside a body of the user to wirelessly transmit stimulus information and power to the internal device inserted in the body of the user in response to the external device receiving the control information, and to cause the data transceiver to transmit the control information to the user terminal,
   wherein the control information includes information used to select a stimulus pattern from at least one stimulus pattern determined in association with a feedback loop including the internal device, the external device, the user terminal, and the electronic device.

4. The medical device method according to claim 1, wherein the transmitted control information is prioritized over a previous control information in response to an input by the user.

* * * * *